(12) United States Patent
Ohdaira

(10) Patent No.: US 10,192,676 B2
(45) Date of Patent: Jan. 29, 2019

(54) NOISE FILTER, MULTISTAGE-CONNECTION LC FILTER, AND MEDICAL INSTRUMENT

(71) Applicant: TOKIN Corporation, Sendai-shi, Miyagi (JP)

(72) Inventor: Yusuke Ohdaira, Sendai (JP)

(73) Assignee: NEC TOKIN CORPORATION, Miyagi (JP)

( * ) Notice: Subject to any disclaimer, the term of this patent is extended or adjusted under 35 U.S.C. 154(b) by 104 days.

(21) Appl. No.: 15/173,277

(22) Filed: Jun. 3, 2016

(65) Prior Publication Data

US 2016/0365192 A1    Dec. 15, 2016

(30) Foreign Application Priority Data

Jun. 12, 2015  (JP) ................. 2015-119155

(51) Int. Cl.
| | |
|---|---|
| *H01F 27/34* | (2006.01) |
| *H03H 1/00* | (2006.01) |
| *A61B 90/00* | (2016.01) |
| *H01F 17/06* | (2006.01) |
| *H01F 27/26* | (2006.01) |
| *H01F 27/40* | (2006.01) |

(52) U.S. Cl.
CPC ............. *H01F 27/34* (2013.01); *A61B 90/00* (2016.02); *H01F 17/062* (2013.01); *H01F 27/266* (2013.01); *H01F 27/40* (2013.01); *H03H 1/0007* (2013.01); *H03H 2001/0035* (2013.01)

(58) Field of Classification Search
CPC ..... A61B 90/00; H01F 17/062; H01F 27/266; H01F 27/34; H01F 27/40; H03H 1/0007; H03H 2001/0035

USPC ......................................................... 333/177
See application file for complete search history.

(56) References Cited

U.S. PATENT DOCUMENTS 5,187,456 A * 2/1993 Hayashi .................. H01F 17/06
                                                            333/181
2003/0078005 A1* 4/2003 Recht ....................... H01F 3/10
                                                            333/12

FOREIGN PATENT DOCUMENTS

| JP | 05-036822    | 5/1993  |
|----|--------------|---------|
| JP | 11-346472    | 12/1999 |
| JP | 2009-267596  | 11/2009 |
| JP | 2010-232245  | 10/2010 |

OTHER PUBLICATIONS

Berman, "All about EMI filters", Electronic Products Magazine, Oct. 1, 2008.*

* cited by examiner

*Primary Examiner* — Benny Lee
*Assistant Examiner* — Hafizur Rahman
(74) *Attorney, Agent, or Firm* — Procopio, Cory, Hargreaves and Savitch LLP

(57) ABSTRACT

A noise filter includes a plurality of inductor elements connected with one another in series. The inductor element includes a ring-shaped magnetic core, a winding wound around the magnetic core, and a ground terminal disposed between the magnetic core and the winding, the ground terminal being connected to a ground. The ground terminal includes a conductive part that surrounds at least a part of an outer periphery of the magnetic core.

12 Claims, 29 Drawing Sheets

NOISE FILTER, MULTISTAGE-CONNECTION LC FILTER, AND MEDICAL INSTRUMENT

INCORPORATION BY REFERENCE

This application is based upon and claims the benefit of priority from Japanese patent application No. 2015-119155, filed on Jun. 12, 2015, the disclosure of which is incorporated herein in its entirety by reference

BACKGROUND OF THE INVENTION

1. Field of the Invention

The present invention relates to a noise filter, a multistage-connection LC filter, and a medical instrument.

2. Description of Related Art

Japanese Unexamined Utility model Application Publication No. 05-036822 discloses a common-mode choke coil in which: a closed magnetic circuit is formed by fixing a UU-shaped or EE-shaped magnetic core by using a U-shaped spring steel; a winding wire (hereinafter simply referred to as a "winding") is wound around this magnetic core; and a pin terminal is connected and fixed to the above-described spring steel, and used as a magnetic core ground terminal. Noise filters including such a common-mode choke coil have been used.

SUMMARY OF THE INVENTION

The present inventors have found the following problem. There has been a demand for noise filters having a high damping characteristic. The above-described noise filters have room for improvement in their damping characteristics.

The present invention provides a noise filter having a high damping characteristic.

A first exemplary aspect of the present invention is a noise filter including a plurality of inductor elements connected with one another in series, in which each of the inductor elements includes: a ring-shaped magnetic core; a winding wound around the magnetic core; and a ground terminal disposed between the magnetic core and the winding, the ground terminal being connected to a ground, and the ground terminal includes a conductive part that surrounds at least a part of an outer periphery of the magnetic core.

According to the above-described configuration, the noise filter has a high damping characteristic.

Further, each of the plurality of inductor elements may be disposed on a respective one of a plurality of support members.

Further, the plurality of inductor elements may be arranged in a row in one direction on one support member.

Further, a plurality of magnetic cores, each of which is included in a respective one of the plurality of inductor elements, may be arranged in a row and the conductive part of the ground terminal may surround at least a part of the plurality of magnetic cores arranged in a row.

Further, the plurality of inductor elements may be stacked on one another on one support member.

Further, the plurality of inductor elements may sandwich a ground conductor plate therebetween.

Further, each of the plurality of inductor elements may be housed in a respective one of a plurality of metal housings.

Further, the plurality of inductor elements may be housed in one metal housing.

Another exemplary aspect of the present invention is a multistage-connection LC filter including:

a plurality of noise filters and a plurality of Y-capacitors, in which the noise filters include a plurality of inductor elements connected with one another in series, each of the inductor elements includes: a ring-shaped magnetic core; a winding wound around the magnetic core; and a ground terminal disposed between the magnetic core and the winding, the ground terminal being connected to a ground, the ground terminal includes a conductive part that surrounds at least a part of an outer periphery of the magnetic core, and the plurality of inductor elements and the plurality of Y-capacitors are alternately connected in series.

Another exemplary aspect of the present invention is a medical instrument including the above-described multistage-connection LC filter according to an aspect of the present invention.

According to the present invention, it is possible to provide a noise filter having a high damping characteristic.

The above and other objects, features and advantages of the present invention will become more fully understood from the detailed description given hereinbelow and the accompanying drawings which are given by way of illustration only, and thus are not to be considered as limiting the present invention.

DESCRIPTION OF THE EXEMPLARY EMBODIMENTS

First Exemplary Embodiment

Figure 1A:
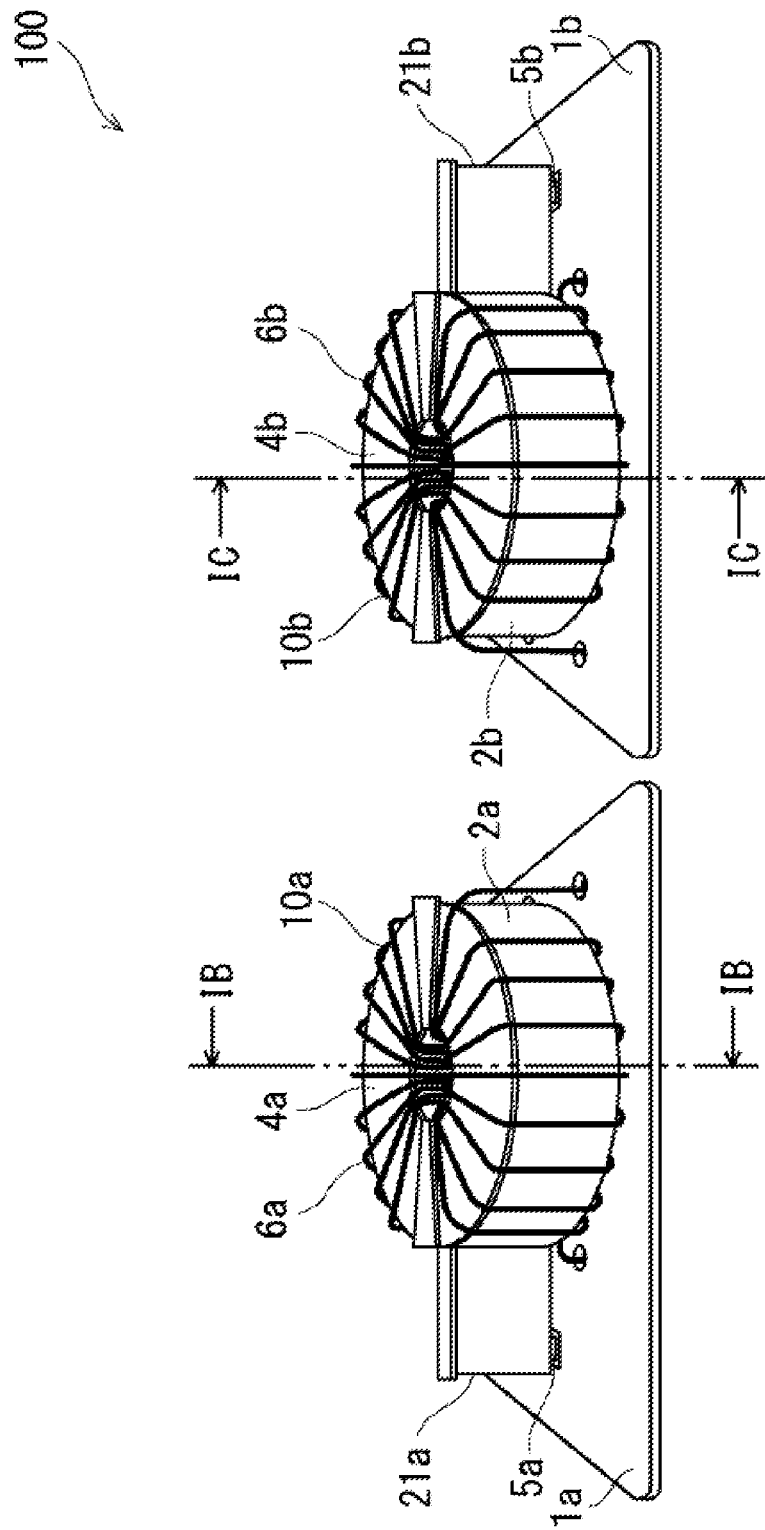
FIG. 1A is a perspective view of a noise filter according to a first exemplary embodiment.
Figure 2:
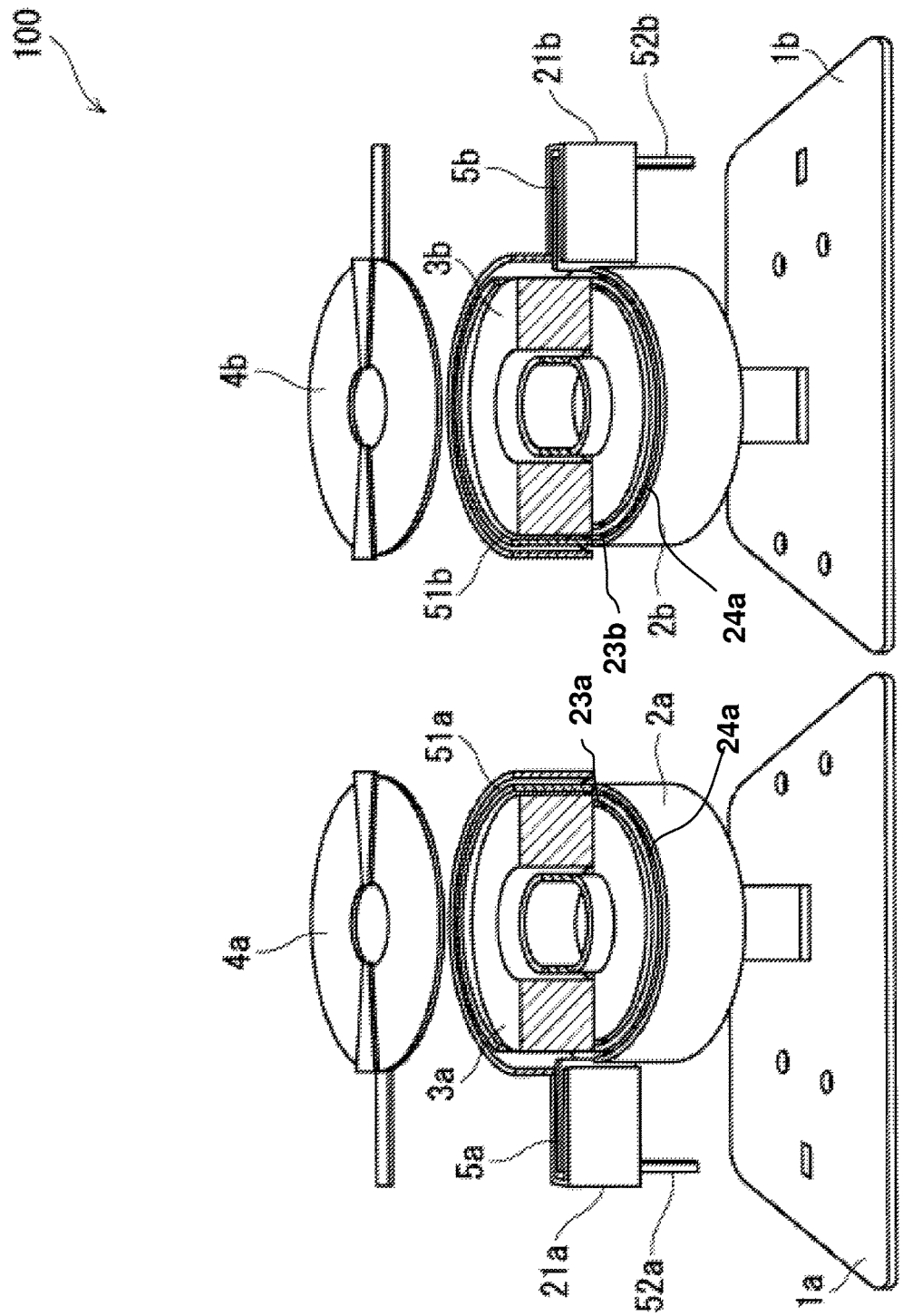
FIG. 2 is an exploded cross section of the noise filter according to the first exemplary embodiment.

A noise filter according to a first exemplary embodiment is explained with reference to FIGS. 1A and 2. FIG. 1A is a perspective view of a noise filter according to the first exemplary embodiment. FIG. 2 is an exploded cross section of the noise filter according to the first exemplary embodiment.

As shown in FIG. 1A, a noise filter 100 includes inductor elements 10a and 10b.

Referring to FIG. 2 in addition to FIG. 1A, the inductor element 10a includes an insulating case 2a, a magnetic core 3a, an insulating cap 4a, a ground terminal 5a, and a winding 6a. Note that the illustrations of the windings 6a and 6b are omitted in FIG. 2 for the sake of easy understanding.

The magnetic core 3a is a ring-shaped member made of ferromagnetic material. The magnetic core 3a has a certain magnetic permeability (herein after simply referred to as "permeability"). Further, the permeability is preferably 5,000 or greater, and more preferably 10,000 or greater.

Figure 1B:
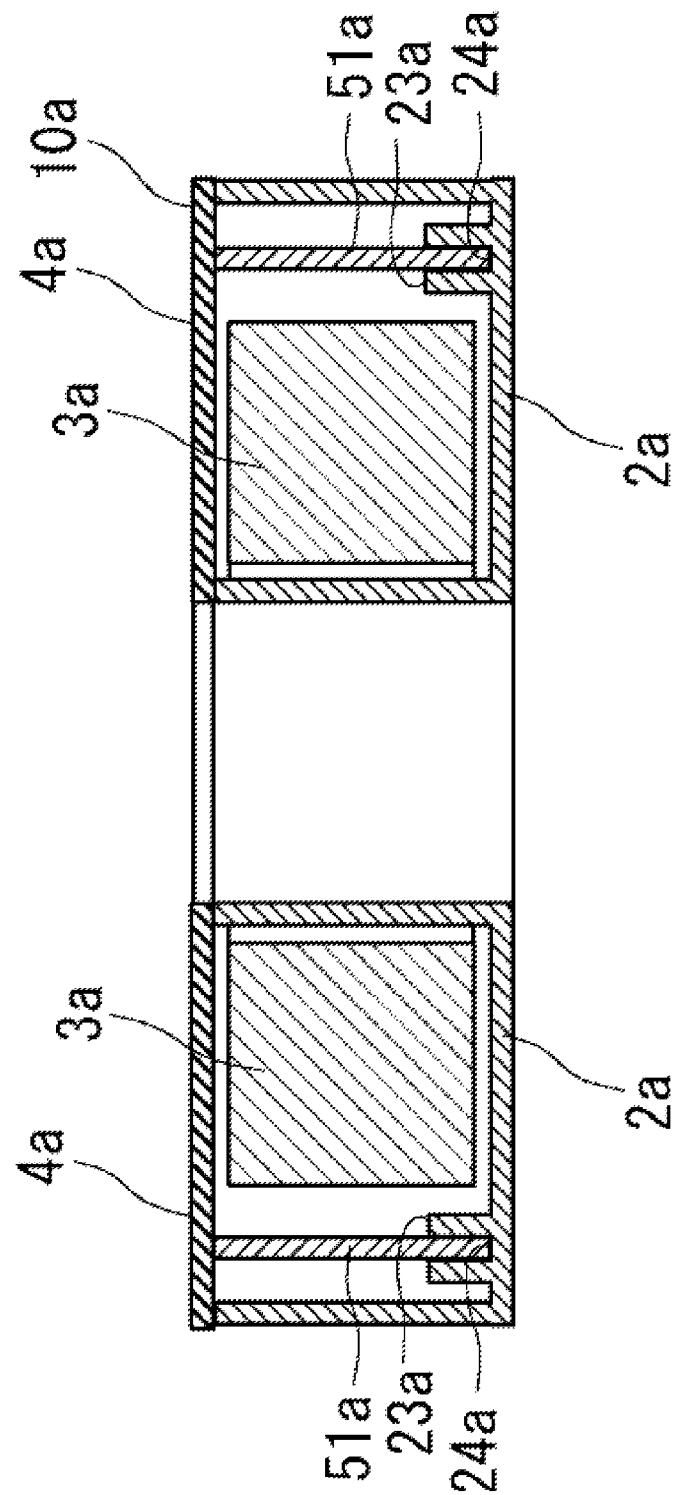
FIG. 1B is a cross section of a main part of an inductor element of the noise filter according to the first exemplary embodiment.

The ground terminal 5a includes a conductive part 51a and a terminal part 52a. The conductive part 51a has such a shape that it surrounds at least a part of the outer periphery of the magnetic core 3a. The conductive part 51a may also surround the top and bottom and the inner periphery of the magnetic core 3a. The terminal part 52a has such a shape that it extends from the conductive part 51a to the outside of the insulating case 2a and is connected to the ground (not shown). The ground terminal 5a is made of, for example, a conductor. The conductive part 51a is, for example, a plate-like part having a curved surface, and the terminal part 52a is, for example, a plate-like part extending in an L-shape. The conductive part 51a is electrically insulated from the magnetic core 3a. For example, the conductive part 51a and the magnetic core 3a may be electrically insulated from each other by disposing a protrusion 23a (see FIG. 1B) which is inserted between the conductive part 51a and the magnetic core 3a or a groove 24a (see FIG. 1B) into which the conductive part 51a is inserted on the inner side of the insulating case 2a and the inner side of the insulating cap 4a. The ground terminal 5a is housed in the insulating case 2a together with the magnetic core 3a.

The insulating case 2a is a ring-shaped housing with an opened top. The insulating case 2a includes an extending part 21a extending in the radial direction of the insulating case 2a. The insulating case 2a houses the magnetic core 3a and the ground terminal 5a, and the extending part 21a covers at least a part of the terminal part 52a of the ground terminal 5a. The insulating cap 4a covers the opening of the insulating case 2a. Note that an upper insulating case and a lower insulating case may be used in place of the insulating case 2a and the insulating cap 4a. The upper and lower insulating cases may be insulating cases that are separated into the upper and lower parts at a part that corresponds to the side wall of the insulating case 2a in the above-described case where the insulating case 2a and the insulating cap 4a are used.

The winding 6a is wound around the magnetic core 3a with the insulating case 2a interposed therebetween. The wire diameter and the number of turns of the winding 6a are selected as appropriate according to the rated current of the apparatus to be manufactured and/or the desired inductance value thereof. Since the winding 6a is connected in series, it is necessary to take account of the rating of the apparatus to be manufactured. However, the wire diameter and the number of turns of the winding 6a may differ from one inductive element to another. By changing the wire diameter and/or the number of turns as appropriate, it is possible to make the designing of a desired common-mode noise damping characteristic more flexible.

The inductor element 10a is mounted on a pedestal 1a. Specifically, the inductor element 10a is mounted on the pedestal 1a in such a manner that the bottom of the insulating case 2a is opposed to or comes into contact with the pedestal 1a. The pedestal 1a fixes the positions of the inductor element 10a, the ground terminal 5a, and the winding 6a.

Similarly to the inductor element 10a, the inductor element 10b includes an insulating case 2b, a magnetic core 3b, an insulating cap 4b, a ground terminal 5b, and a winding 6b.

The magnetic core 3b is a ring-shaped member made of ferromagnetic material. The magnetic core 3b has a certain magnetic permeability, and the permeability is preferably 5,000 or greater, and more preferably 10,000 or greater.

Figure 1C:
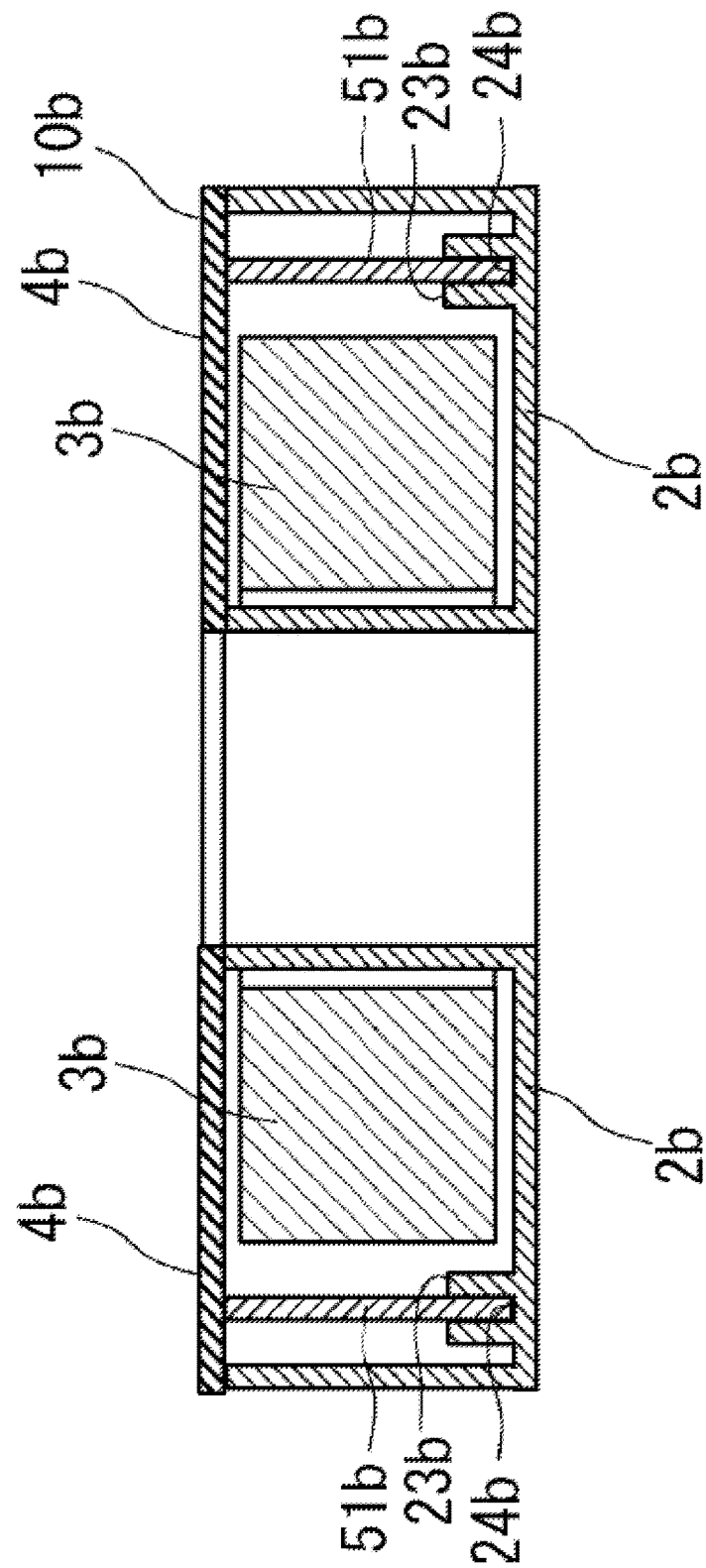
FIG. 1C is a cross section of a main part of another inductor element of the noise filter according to the first exemplary embodiment.

The ground terminal 5b includes a conductive part 51b and a terminal part 52b. The conductive part 51b has such a shape that it surrounds at least a part of the outer periphery of the magnetic core 3b. The conductive part 51b may also surround the top and bottom and the inner periphery of the magnetic core 3b. The terminal part 52b has such a shape that it extends from the conductive part 51b to the outside of the insulating case 2b and is connected to the ground (not shown). The ground terminal 5b is made of, for example, a conductor. The conductive part 51b is, for example, a plate-like part having a curved surface, and the terminal part 52b is, for example, a plate-like part extending in an L-shape. The conductive part 51b is electrically insulated from the magnetic core 3b. For example, the conductive part 51b and the magnetic core 3b may be electrically insulated from each other by disposing a protrusion 23b (see FIG. 1C) which is inserted between the conductive part 51b and the magnetic core 3b or a groove 24b (see FIG. 1C) into which the conductive part 51b is inserted on the inner side of the insulating case 2b and the inner side of the insulating cap 4b. The ground terminal 5b is housed in the insulating case 2b together with the magnetic core 3b.

The insulating case 2b is a ring-shaped housing with an opened top. The insulating case 2b includes an extending part 21b extending in the radial direction of the insulating case 2b. The insulating case 2b houses the magnetic core 3b and the ground terminal 5b, and the extending part 21b covers at least a part of the terminal part 52b of the ground terminal 5b. The insulating cap 4b covers the opening of the insulating case 2b. Note that an upper insulating case and a lower insulating case may be used in place of the insulating case 2b and the insulating cap 4b. The upper and lower insulating cases may be insulating cases that are separated into the upper and lower parts at a part that corresponds to the side wall of the insulating case 2b in the above-described case where the insulating case 2b and the insulating cap 4b are used.

The winding 6b is wound around the magnetic core 3b with the insulating case 2b interposed therebetween. The wire diameter and the number of turns of the winding 6b are selected as appropriate according to the rated current of the apparatus to be manufactured and/or the desired inductance value thereof. Since the winding 6b is connected in series, it is necessary to take account of the rating of the apparatus to be manufactured. However, the wire diameter and the number of turns of the winding 6b may differ from one inductive element to another. By changing the wire diameter and/or the number of turns as appropriate, it is possible to make the designing of a desired common-mode noise damping characteristic more flexible.

The inductor element 10b is mounted on a pedestal 1b. Specifically, the inductor element 10b is mounted on the pedestal 1b in such a manner that the bottom of the insulating case 2b is opposed to or comes into contact with the pedestal 1b. The pedestal 1b fixes the positions of the inductor element 10b, the ground terminal 5b, and the winding 6b.

The inductors elements 10a and 10b are mounted on their respective pedestals (i.e., mutually-different pedestals), thus giving high flexibility to their mounting method. For example, the inductors elements 10a and 10b may be disposed adjacent to each other on the same plane, disposed with a certain distance therebetween on the same plane, or disposed on their respective planes having different heights. Further, in FIGS. 1A and 2, the extending part 21a extends in the direction opposite to the direction in which the extending part 21b extends. However, the extending part 21a may extend in various directions with respect to the direction in which the extending part 21b extends. For example, the extending part 21a may extend in a direction that differs from the direction in which extending part 21b extends by 90° or extend in the same direction as the direction in which the extending part 21b extends.

Note that the magnetic core 3b may be formed by using material different from that for the magnetic core 3a. For example, there is a case where the maximum permeability of one of the magnetic cores 3a and 3b is lower than that of the other magnetic core and this one of the magnetic cores 3a and 3b is made of material that maintains a certain permeability over a wide frequency range. Such a case is preferable because the common-mode noise can be removed over a wider frequency band. The windings 6a and 6b may be connected to each other in series.

Note that when the noise filter is incorporated into a certain circuit or the like and a current is feed to the noise filter, the ground terminals 5a and 5b form a capacity as in the case of a Y-capacitor and the common-mode noise is dissipated into the ground. As a result, the noise can be considerably attenuated (i.e., dumped). Further, since the noise filter does not require any Y-capacitor, the leak current is small.

As described above, the noise filter according to the first exemplary embodiment has a high damping characteristic. Further, since the inductor elements are mounted on their respective pedestals (i.e., mutually-different pedestals), they can be mounted independently of each other and have an excellent mounting property.

Second Exemplary Embodiment

Figure 3:
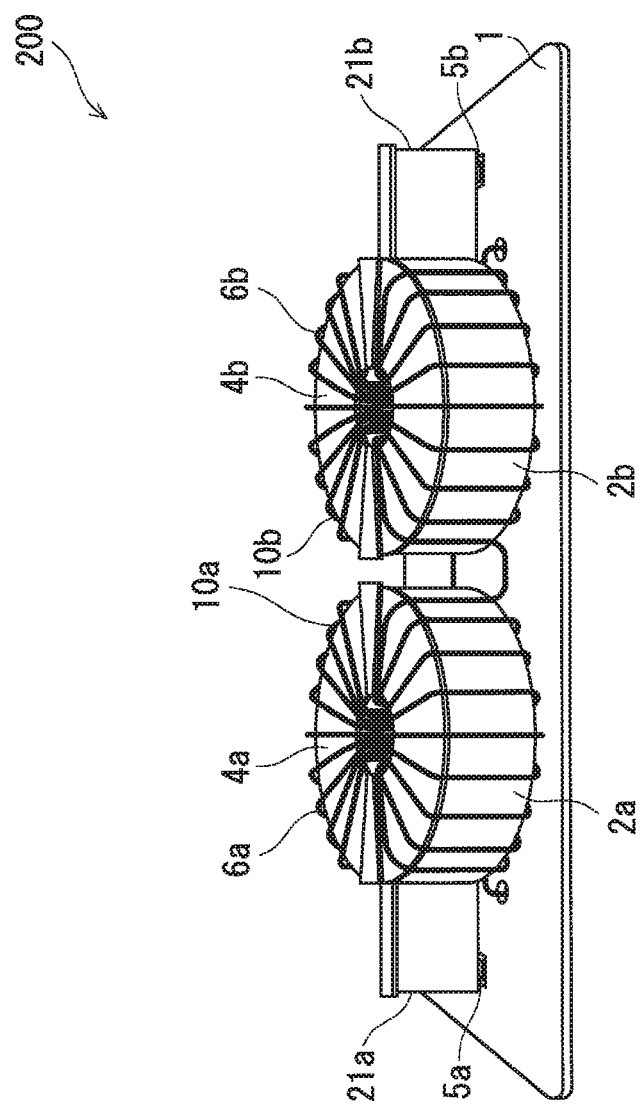
FIG. 3 is a perspective view of a noise filter according to a second exemplary embodiment.
Figure 4:
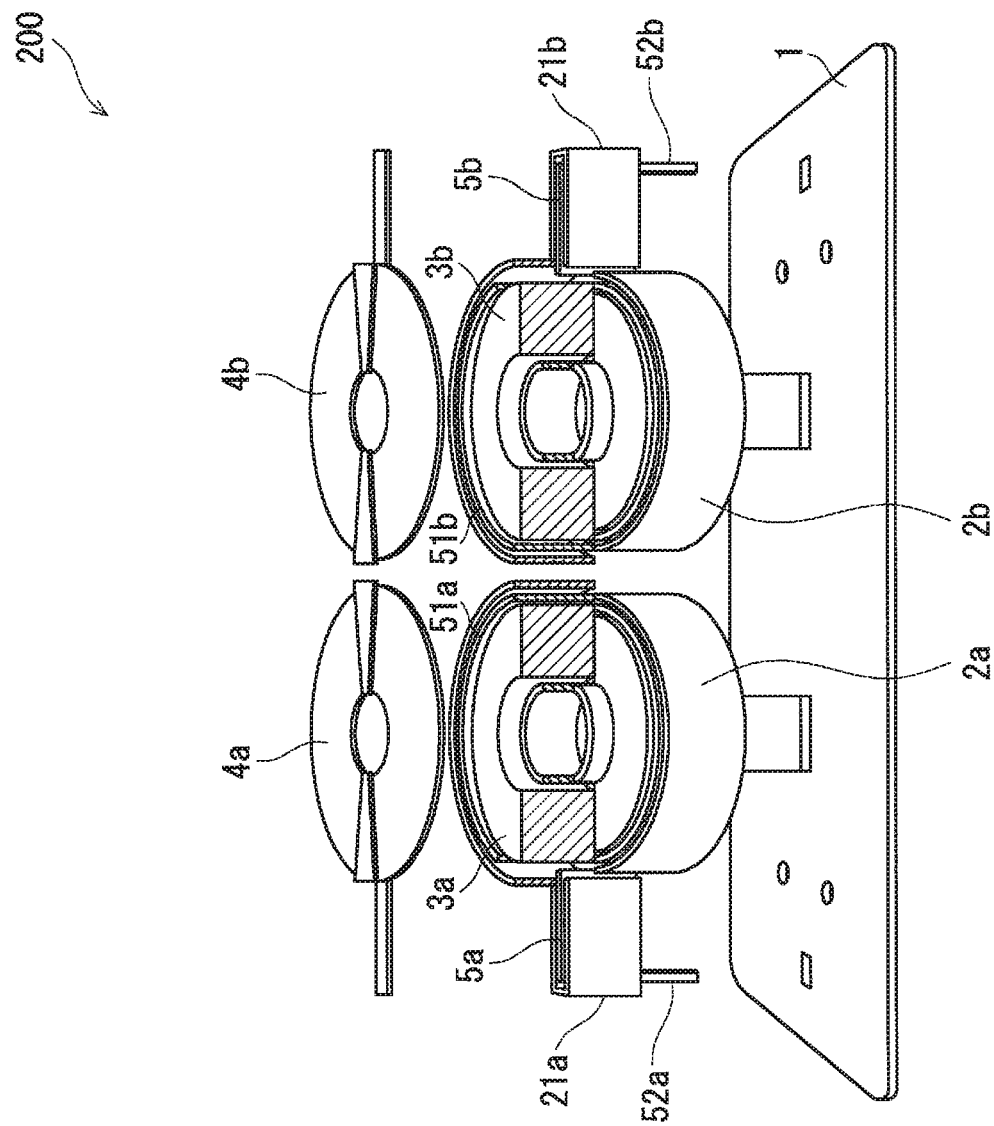
FIG. 4 is an exploded cross section of the noise filter according to the second exemplary embodiment.

Next, a noise filter according to a second exemplary embodiment is explained with reference to FIGS. 3 and 4. FIG. 3 is a perspective view of a noise filter according to the second exemplary embodiment. FIG. 4 is an exploded cross section of the noise filter according to the second exemplary embodiment. Note that the illustrations of the windings 6a and 6b are omitted in FIG. 4 for the sake of easy understanding. The configuration of the noise filter according to the second exemplary embodiment is the same as that of the first exemplary embodiment except for the pedestals and the connection between the wirings. The parts of the configuration of the second exemplary embodiment different from those of the first exemplary embodiment are explained hereinafter while the explanations of the same parts are omitted as appropriate.

As shown in FIGS. 3 and 4, a noise filter 200 includes a pedestal 1. The inductors elements 10a and 10b are arranged side by side (i.e., arranged in a row) on the pedestal 1. The windings 6a and 6b are connected to each other in series.

As described above, similarly to the noise filter according to the first exemplary embodiment, the noise filter according to the second exemplary embodiment includes ground terminals and has a high damping characteristic. Further, two inductor elements are disposed on the same pedestal. Therefore, the noise filter according to the second exemplary embodiment can be easily manufactured.

Third Exemplary Embodiment

Figure 5:
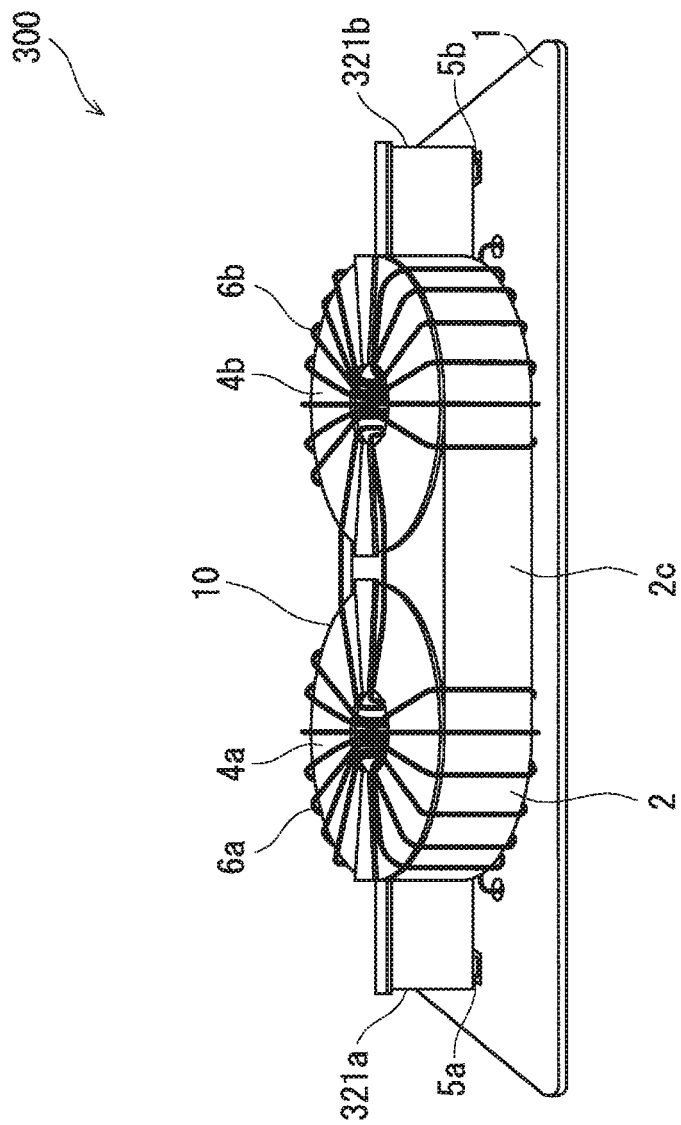
FIG. 5 is a perspective view of a noise filter according to a third exemplary embodiment.
Figure 6:
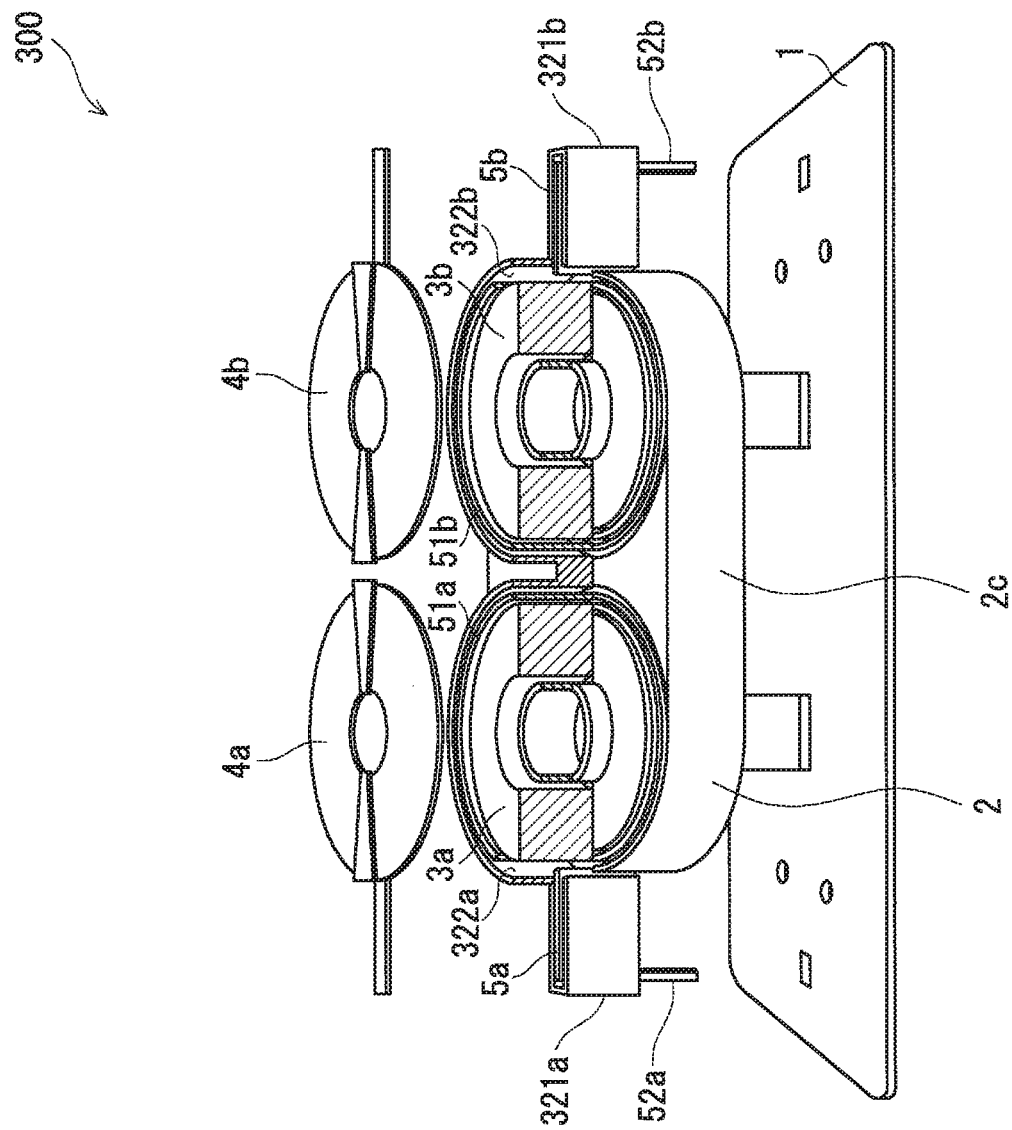
FIG. 6 is an exploded cross section of the noise filter according to the third exemplary embodiment.

Next, a noise filter according to a third exemplary embodiment is explained with reference to FIGS. 5 and 6. FIG. 5 is a perspective view of a noise filter according to the third exemplary embodiment. FIG. 6 is an exploded cross section of the noise filter according to the third exemplary embodiment. Note that the illustrations of the windings 6a and 6b are omitted in FIG. 6 for the sake of easy understanding. The configuration of the noise filter according to the third exemplary embodiment is the same as that of the second exemplary embodiment except for the insulating case. The parts of the configuration of the third exemplary embodiment different from those of the second exemplary embodiment are explained hereinafter while the explanations of the same parts are omitted as appropriate.

As shown in FIGS. 5 and 6, a noise filter 300 includes an insulating case 2. The insulating case 2 has a shape identical to the shape of the case that is formed by integrating the insulating cases 2a and 2b (see FIG. 1A) with each other. For example, the insulating case 2 includes a reinforcement part 2c that mechanically connects the insulating cases 2a and 2b with each other so that the outer peripheral surfaces of the insulating cases 2a and 2b are integrated with each other more strongly. Further, the insulating case 2 may have a shape identical to the shape of the one that is formed by disposing the insulating cases 2a and 2b (see FIG. 1A) side by side on the same plane and joining the outer peripheral surfaces of the insulating cases 2a and 2b with each other.

The insulating case 2 is a housing with an opened top and includes extending parts 321a and 321b and accommodation parts 322a and 322b.

The accommodation part 322a houses the magnetic core 3a and the ground terminal 5a, and the extending part 321a covers at least a part of the terminal part 52a of the ground terminal 5a.

Similarly, the accommodation part 322b houses the magnetic core 3b and the ground terminal 5b, and the extending part 321b covers at least a part of the terminal part 52b of the ground terminal 5b.

The insulating caps 4a and 4b cover the opening of the insulating case 2.

The windings 6a and 6b are connected to each other in series.

As described above, similarly to the noise filter according to the first exemplary embodiment, the noise filter according to the third exemplary embodiment includes the ground terminals and has a high damping characteristic. Further, the two inductor elements are housed in the same insulating case. Therefore, the noise filter according to the third exemplary embodiment can be easily manufactured.

Fourth Exemplary Embodiment

Figure 7A:
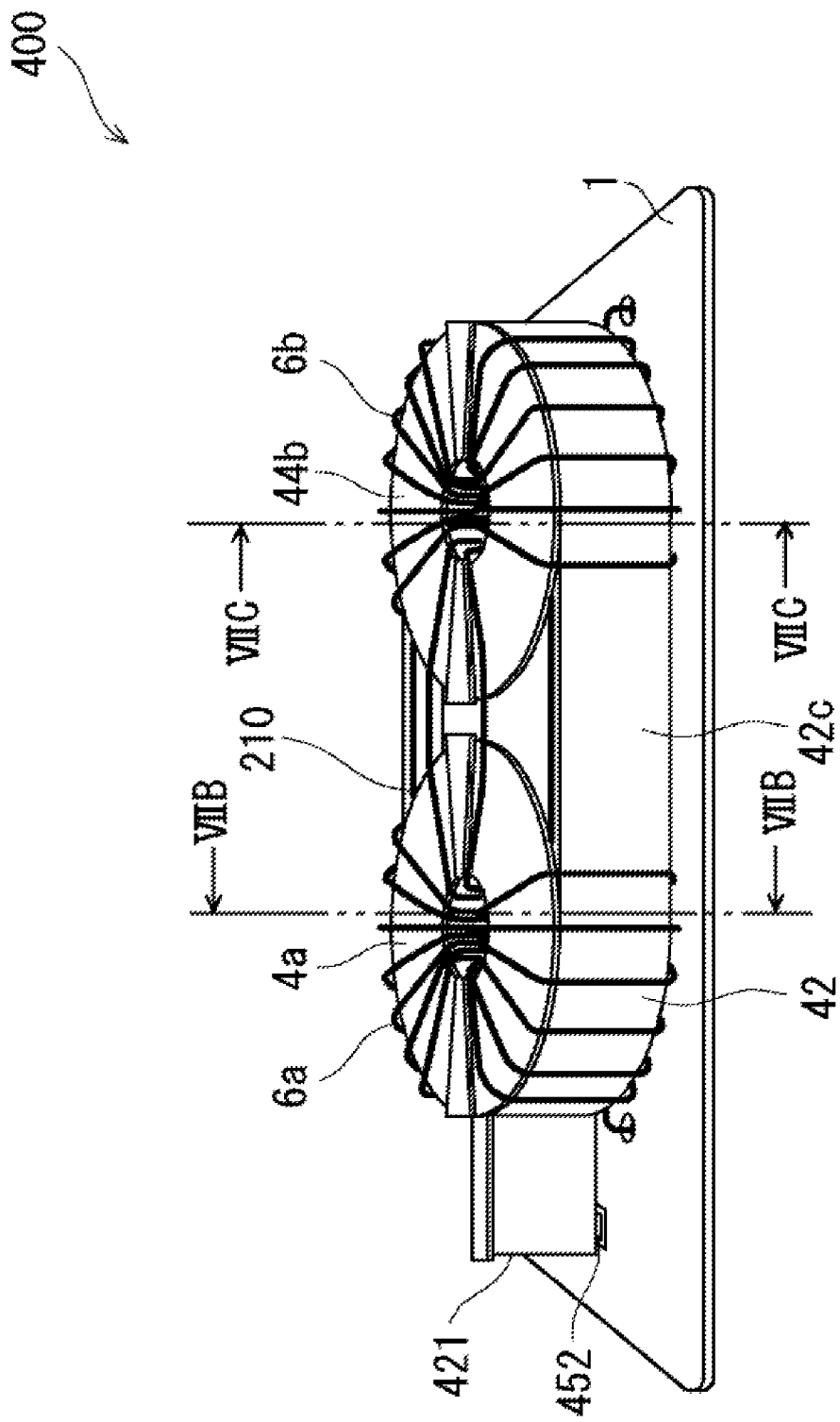
FIG. 7A is a perspective view of a noise filter according to a fourth exemplary embodiment.
Figure 8:
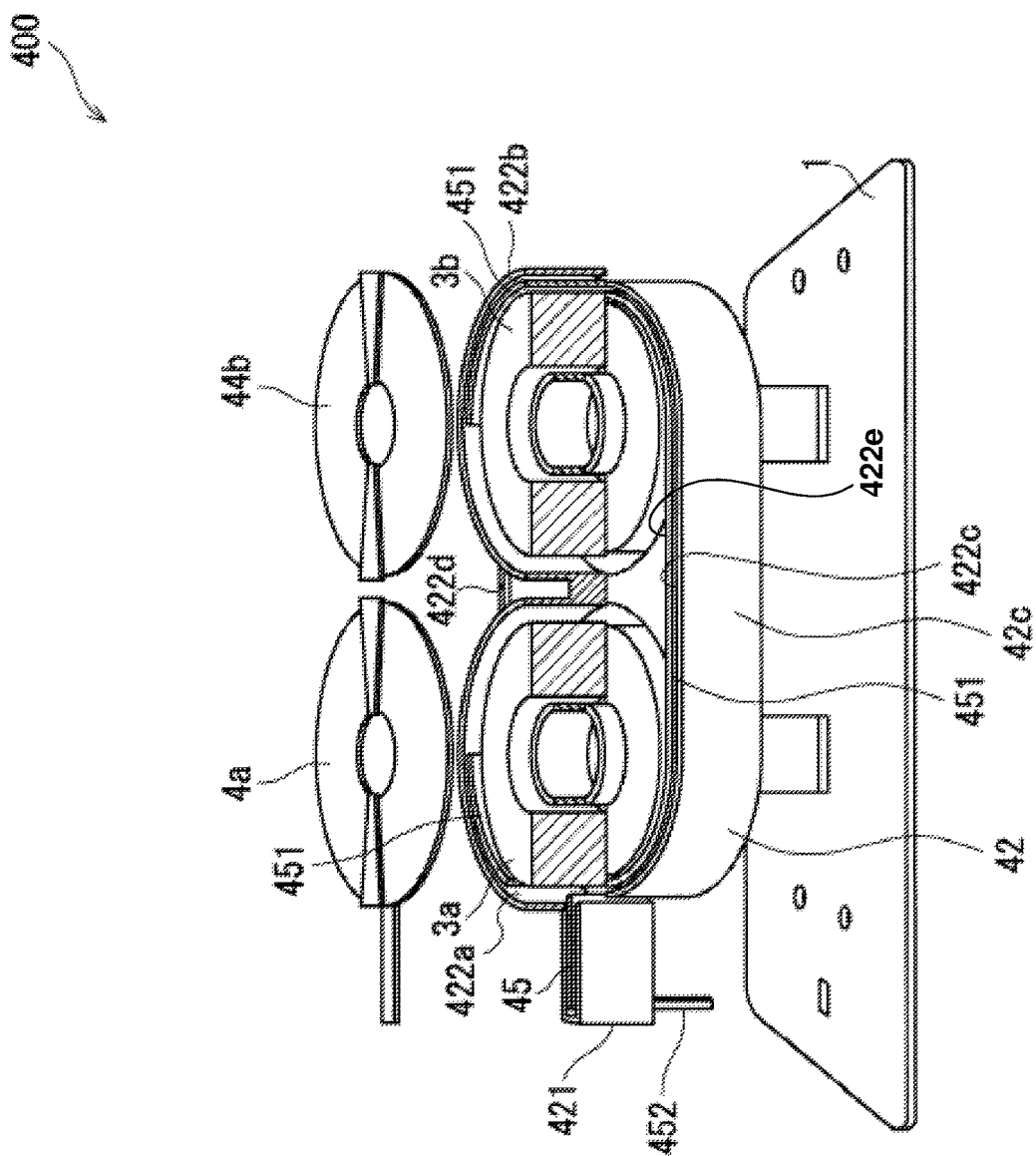
FIG. 8 is an exploded cross section of the noise filter according to the fourth exemplary embodiment.

Next, a noise filter according to a fourth exemplary embodiment is explained with reference to FIGS. 7A and 8. FIG. 7A is a perspective view of a noise filter according to the fourth exemplary embodiment. FIG. 8 is an exploded cross section of the noise filter according to the fourth exemplary embodiment. Note that the illustrations of the windings 6a and 6b are omitted in FIG. 8 for the sake of easy understanding. The configuration of the noise filter according to fourth exemplary embodiment is the same as that of the third exemplary embodiment except for the ground terminal and the insulating case. The parts of the configuration of the fourth exemplary embodiment different from those of the third exemplary embodiment are explained hereinafter while the explanations of the same parts are omitted as appropriate.

As shown in FIGS. 7A and 8, a noise filter 400 includes a ground terminal 45 and an insulating case 42.

Figure 7B:
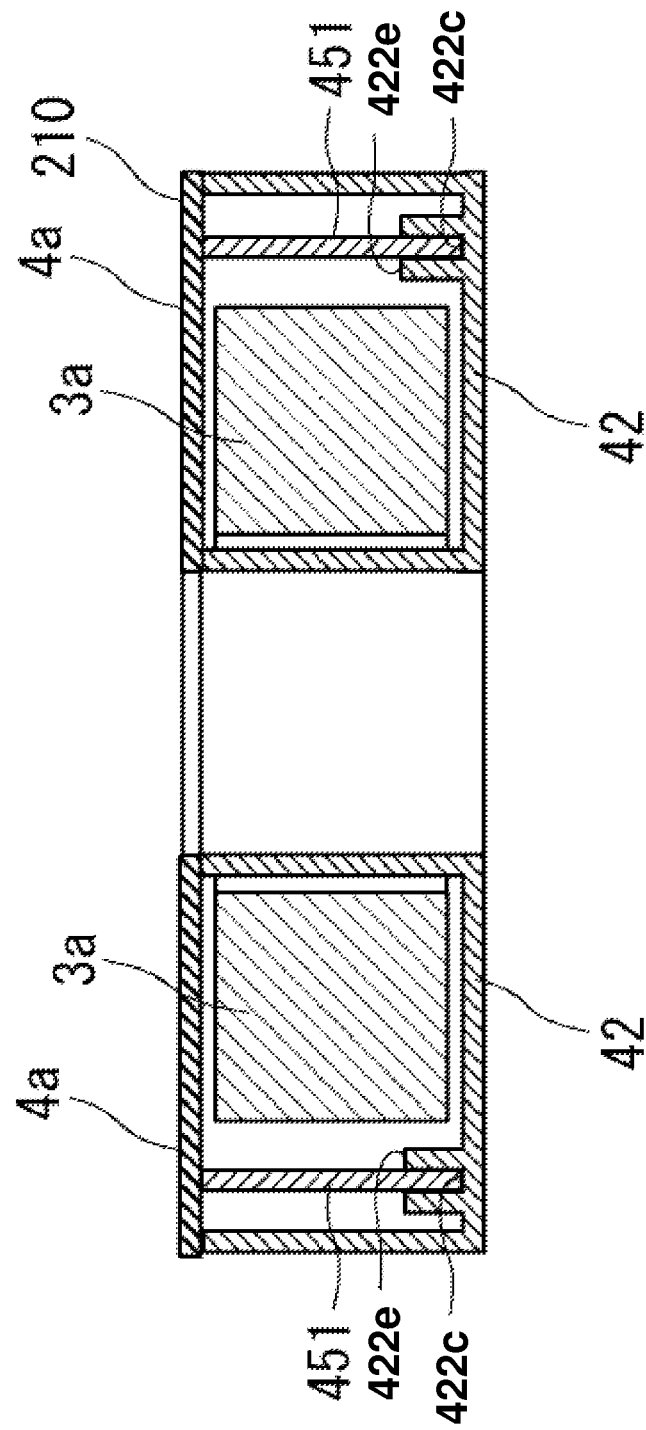
FIG. 7B is a cross section of a part of the noise filter according to the fourth exemplary embodiment.
Figure 7C:
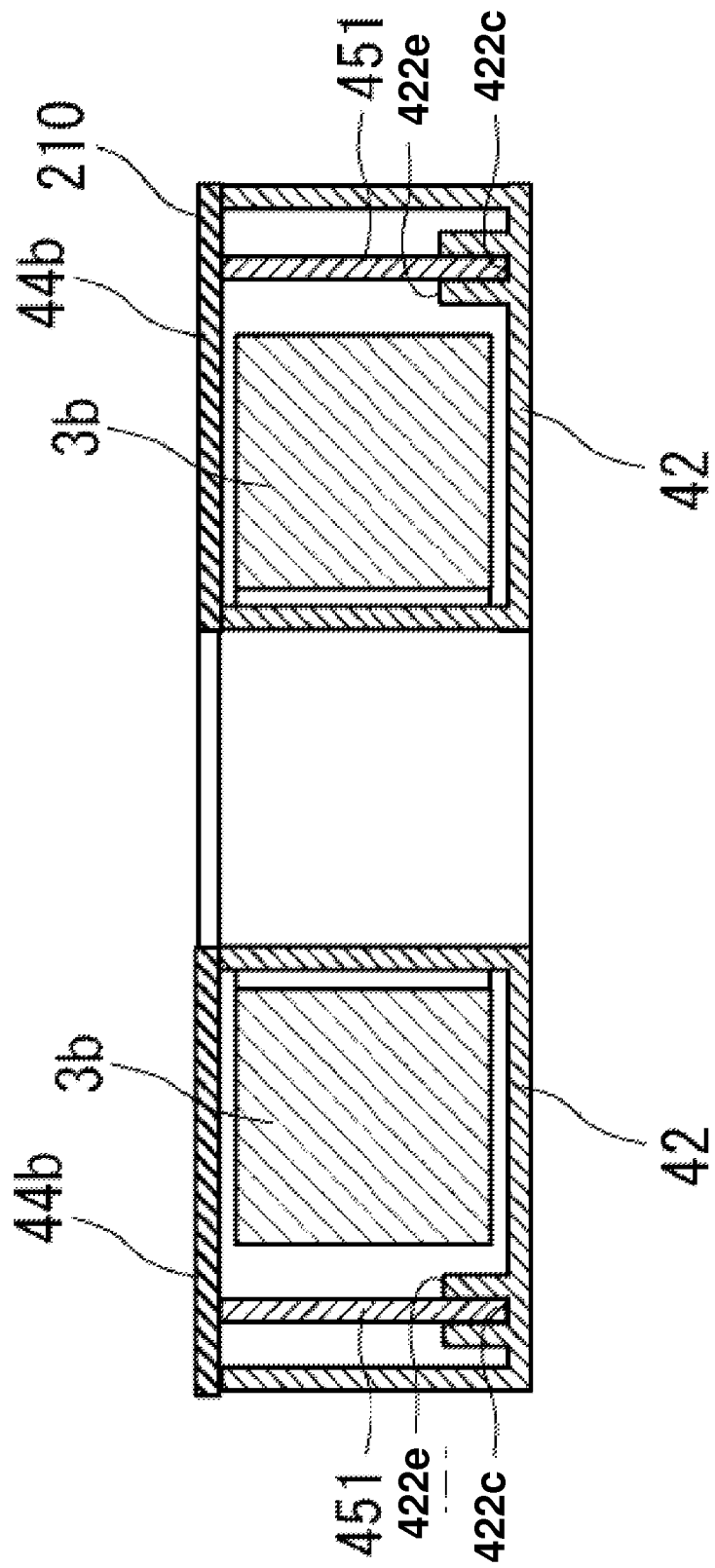
FIG. 7C is a cross section of another part of the noise filter according to the fourth exemplary embodiment.

The ground terminal 45 includes a conductive part 451 that surrounds at least a part of the outer periphery of the magnetic cores 3a and 3b, which are arranged side by side, and a terminal part 452 that extends from the conductive part 451 to the outside of the insulating case 42 and is connected to the ground (not shown). The ground terminal 45 is, for example, a plate having a curved-surface made of a conductive body. The conductive part 451 is electrically insulated from the magnetic cores 3a and 3b. For example, the conductive part 451 and the magnetic cores 3a and 3b may be electrically insulated from each other by disposing a protrusion 423 (see FIG. 7B) which is inserted between the conductive part 451 and the magnetic core 3a or a groove 424 (see FIG. 7B and FIG. 7C) into which the conductive part 451 is inserted on the inner side of the insulating case 42 and the inner side of the insulating caps 4a and 44b. The ground terminal 45 is housed in the insulating case 42 together with the magnetic cores 3a and 3b.

The insulating case 42 has a shape identical to the shape of the case that is formed by integrating the insulating cases 2a and 2b (see FIG. 1A) with each other. For example, the insulating case 42 may have a shape identical to the shape of the one that is formed by disposing the insulating cases 2a and 2b side by side on the same plane and joining the outer peripheral surfaces of the insulating cases 2a and 2b with each other. Further, the insulating case 42 may include a reinforcement part 42c that mechanically connects the insulating cases 2a and 2b with each other so that the outer peripheral surfaces of the insulating cases 2a and 2b are integrated with each other more strongly.

The insulating case 42 is a housing with an opened top and includes accommodation parts 422a, 422b, 422c and 422d, and an extending part 421.

The accommodation part 422a houses the magnetic core 3a and the extending part 421 covers at least a part of the terminal part 452 of the ground terminal 45.

The accommodation part 422b houses the magnetic core 3b.

The accommodation parts 422c and 422d are disposed between the accommodation parts 422a and 422b and thereby connect the accommodation part 422a with the accommodation part 422b.

The conductive part 451 is housed by the accommodation parts 422a, 422b, 422c and 422d.

The insulating caps 4a and 44b cover the opening of the insulating case 42.

The windings 6a and 6b are connected to each other in series.

As described above, similarly to the noise filter according to the first exemplary embodiment, the noise filter according to the fourth exemplary embodiment includes ground terminals and has a high damping characteristic. Further, a capacity is formed by using one ground terminal for two inductor elements. Therefore, the noise filter according to the fourth exemplary embodiment can be easily manufactured.

Fifth Exemplary Embodiment

Figure 9:
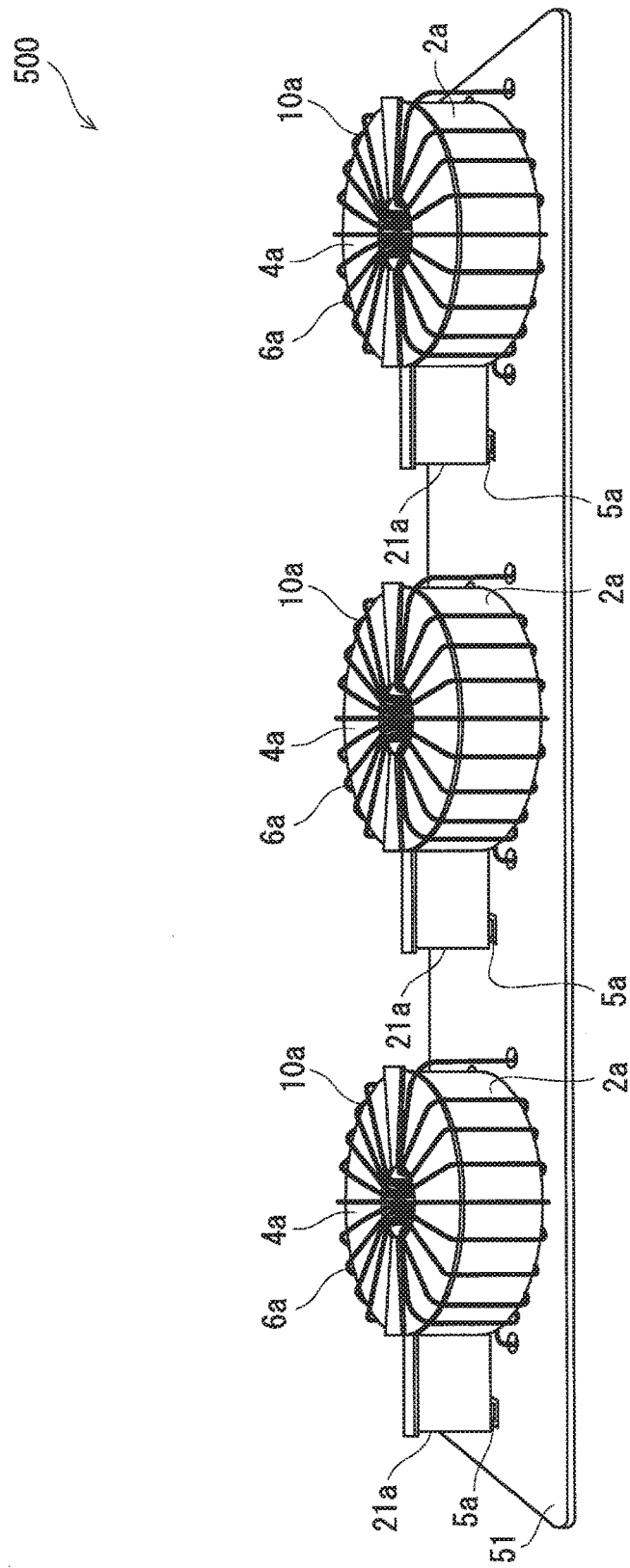
FIG. 9 is a perspective view of a noise filter according to a fifth exemplary embodiment.

Next, a noise filter according to a fifth exemplary embodiment is explained with reference to FIG. 9. FIG. 9 is a perspective view of a noise filter according to the fifth exemplary embodiment. The noise filter according to the fifth exemplary embodiment includes a configuration that is the same as that of the noise filter according to the first exemplary embodiment. The parts of the configuration of the fifth exemplary embodiment different from those of the first exemplary embodiment are explained hereinafter while the explanations of the same parts are omitted as appropriate.

As shown in FIG. 9, a noise filter 500 includes three inductor elements 10a and a pedestal 51. The three inductor elements 10a are arranged in a row in one direction on the pedestal 51. The windings 6a, each of which is included in a respective one of the three inductor elements 10a, are connected in series.

As described above, similarly to the noise filter according to the first exemplary embodiment, the noise filter according to the fifth exemplary embodiment includes ground terminals and has a high damping characteristic. Further, three inductor elements are disposed on one pedestal and connected in series. As a result, the noise filter according to the fifth exemplary embodiment can have a damping characteristic comparable to that of a multistage-connection LC filter in which three LC filters are connected in series.

Sixth Exemplary Embodiment

Figure 10:
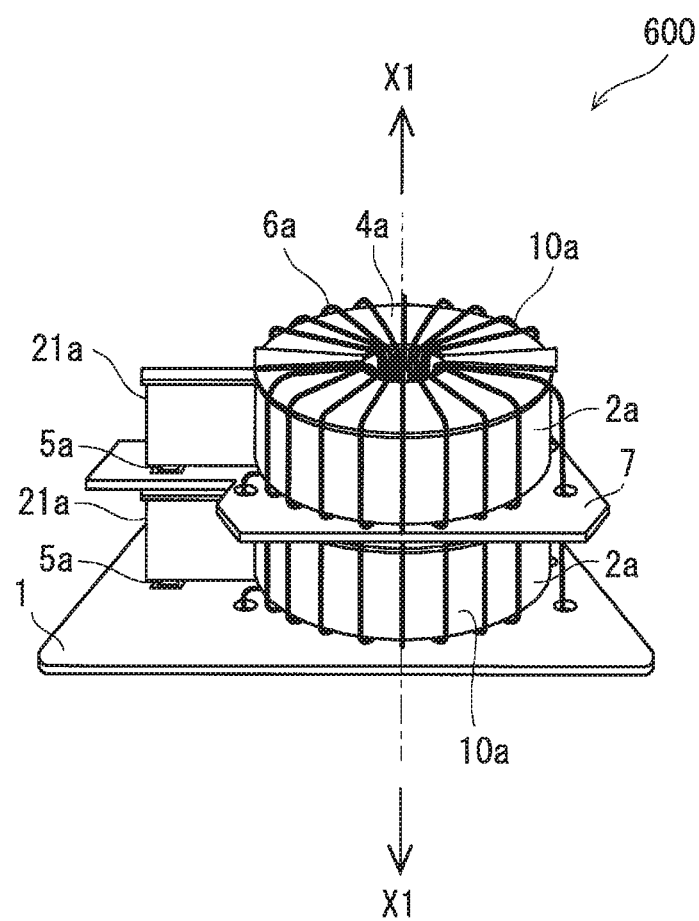
FIG. 10 is a perspective view of a noise filter according to a sixth exemplary embodiment.

Next, a noise filter according to a sixth exemplary embodiment is explained with reference to FIG. 10. FIG. 10 is a perspective view of a noise filter according to the sixth exemplary embodiment. The noise filter according to the sixth exemplary embodiment includes a configuration that is the same as that of the noise filter according to the first exemplary embodiment. The parts of the configuration of the sixth exemplary embodiment different from those of the first exemplary embodiment are explained hereinafter while the explanations of the same parts are omitted as appropriate.

As shown in FIG. 10, a noise filter 600 includes two inductor elements 10a, a pedestal 1, and a ground conductor plate 7. The two inductor elements 10a are stacked on one another in the vertical direction on the pedestal 1. The two inductor elements 10a sandwich the ground conductor plate 7 therebetween. The ground terminal 5a and the ground conductor plate 7 may be joined with each other by, for example, soldering or the like. Specifically, an axis X1 of the inductor elements 10a intersects the pedestal 1 and may be substantially perpendicular to the pedestal 1. Further, as viewed from the above the pedestal 1, the two stacked inductor elements 10a may overlap each other. The windings 6a, each of which is included in a respective one of the two inductor elements 10a, are connected in series.

As described above, similarly to the noise filter according to the first exemplary embodiment, the noise filter according to the sixth exemplary embodiment includes the ground terminals and has a high damping characteristic. Further, since two inductor elements are stacked on one another in the vertical direction on one pedestal, the necessary area in which the noise filter is mounted can be reduced. Further, the ground conductor plate is interposed between the two inductor elements. Therefore, even if a current that conducts capacitive coupling between the respective coils of the two inductor elements occurs, this capacitive coupling is cut off by the ground conductor plate. As a result, the noise filter has a high damping characteristic in different frequency bands.

Seventh Exemplary Embodiment

Figure 11:
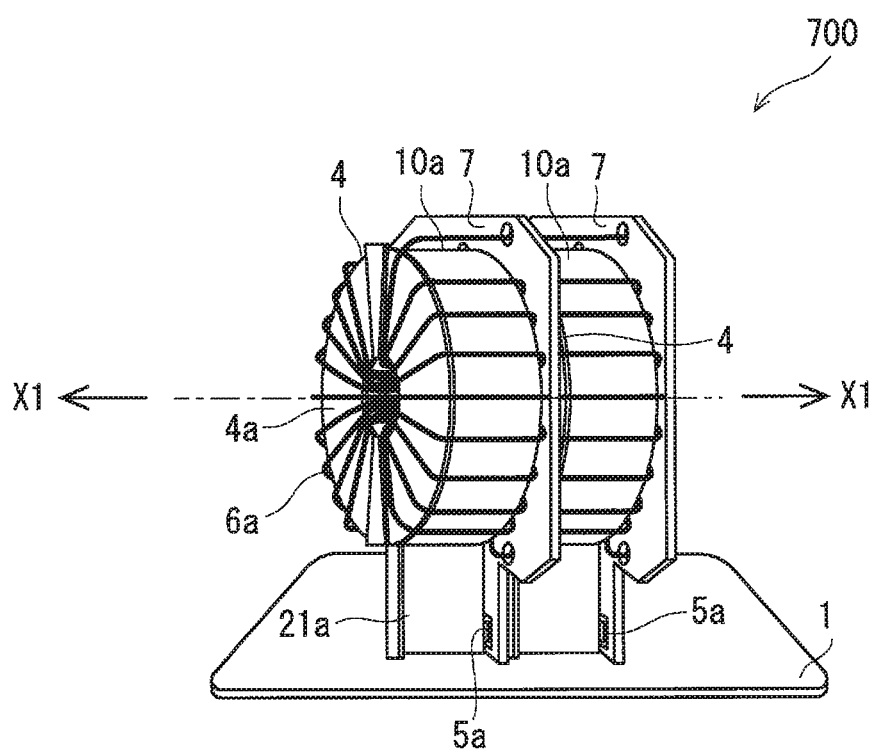
FIG. 11 is a perspective view of a noise filter according to a seventh exemplary embodiment.

Next, a noise filter according to a seventh exemplary embodiment is explained with reference to FIG. 11. FIG. 11 is a perspective view of a noise filter according to the seventh exemplary embodiment. The noise filter according to the seventh exemplary embodiment includes a configuration that is the same as that of the noise filter according to the first exemplary embodiment. The parts of the configuration of the seventh exemplary embodiment different from those of the first exemplary embodiment are explained hereinafter while the explanations of the same parts are omitted as appropriate.

As shown in FIG. 11, a noise filter 700 includes two inductor elements 10a, a pedestal 1, and a ground conductor plate 7. The two inductor elements 10a are stacked on one another in a horizontal direction on the pedestal 1. The inductor elements 10a sandwich the ground conductor plate 7 therebetween. The ground terminals 5a, each of which is included in a respective one of the two inductor elements 10a, may be joined with the ground conductor plate 7 by, for example, soldering or the like. Specifically, (parts of) the outer peripheral surfaces of the inductor elements 10a are opposed to the pedestal 1. An axis X1 of the inductor elements 10a may be substantially in parallel with the pedestal 1. Further, as viewed in a direction in parallel with the pedestal 1, the two stacked inductor elements 10a may overlap each other. The windings 6a, each of which is included in a respective one of the two inductor elements 10a, are connected in series.

As described above, similarly to the noise filter according to the first exemplary embodiment, the noise filter according to the seventh exemplary embodiment includes the ground terminals and has a high damping characteristic. Further, since two inductor elements are stacked on one another in the horizontal direction, the necessary area in which the noise filter is mounted can be reduced. Further, the ground conductor plate is interposed between the two inductor elements. Therefore, even if a current that conducts capacitive coupling between the respective coils of the two inductor elements occurs, this capacitive coupling is cut off by the ground conductor plate. As a result, the noise filter has a high damping characteristic in different frequency bands.

Note that although each of the noise filters according to the above-described first to seventh exemplary embodiments includes two or three inductor elements, the noise filter may include four or more inductor elements. These four or more inductor elements are preferably connected with one another in series. Further, although each of the noise filters according to the above-described first to seventh exemplary embodiments includes the pedestal, the noise filter may be mounted on any type of a support member that can support inductor elements. Examples of the support member include a substrate.

Further, although each of the noise filters according to the above-described sixth and seventh exemplary embodiments includes the ground conductor plate interposed between two inductor elements, the ground conductor plate may be omitted as required.

Note that an LC filter or a multistage-connection LC filter may be formed by using inductor elements included in the noise filter according to above-described first to seventh exemplary embodiments. Such an LC filter can be formed by alternately connecting a plurality of inductor elements included in the noise filter according to above-described first to seventh exemplary embodiments and a plurality of Y-capacitors with one another in series. Further, such a multistage-connection LC filter may be formed by connecting a plurality of LC filters, each of which has the above-described configuration, with one another in series. Examples of the multistage-connection LC filter include a two-stage-connection LC filter, a three-stage-connection LC filter, a four-stage-connection LC filter and so on.

Figure 22:
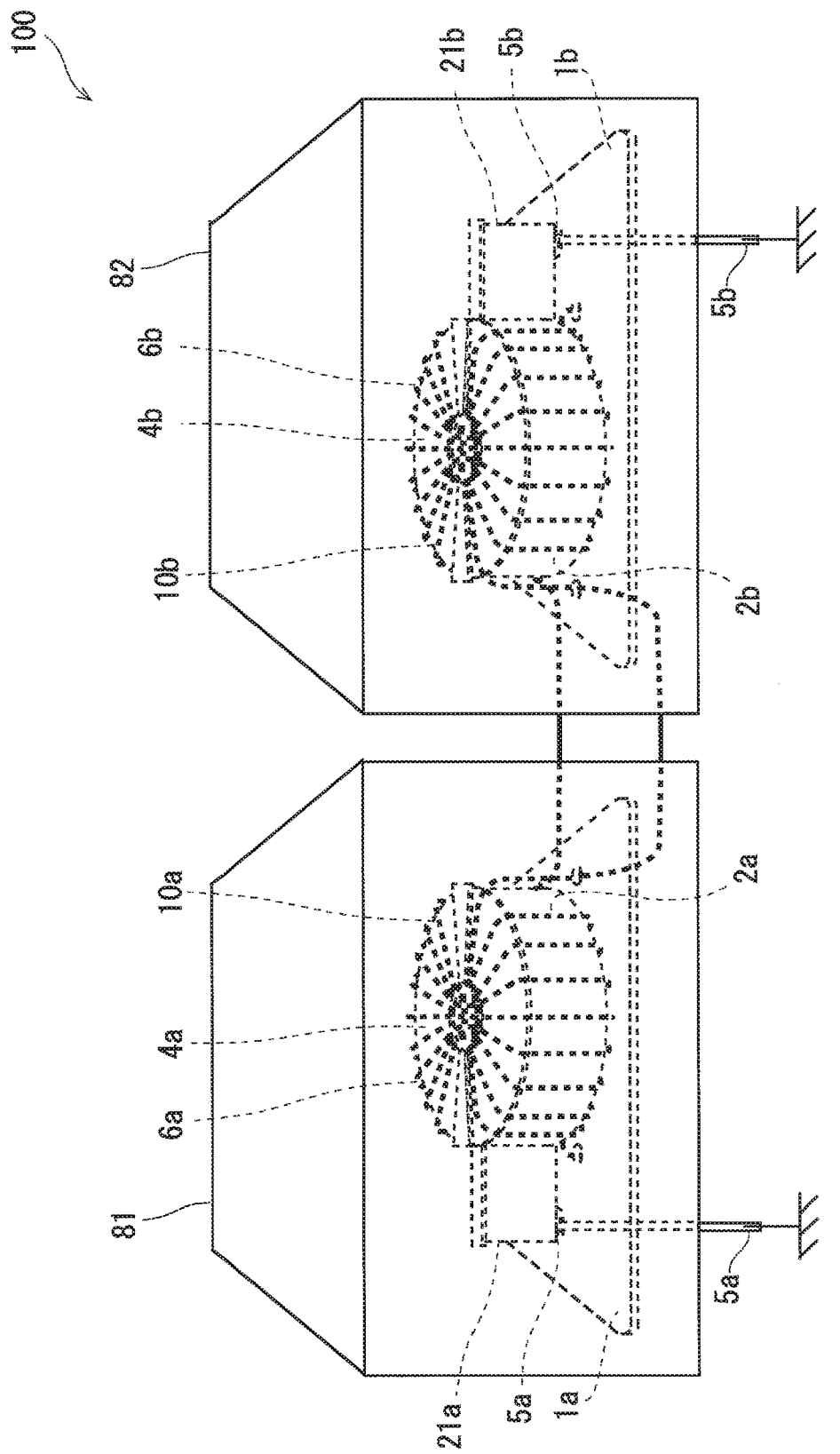
FIG. 22 is a perspective view of a modified example of the noise filter according to the first exemplary embodiment.

Further, as shown in FIG. 22, the noise filter 100 according to the above-described first exemplary embodiment may further include two metal housings 81 and 82 that house the inductor elements 10a and 10b, respectively. Specifically, the metal housing 81 houses the inductor element 10a and the pedestal 1a. The metal housing 82 houses the inductor element 10b and the pedestal 1b. When the noise filter 100 includes the metal housings 81 and 82, the ground terminals 5a and 5b and the metal housings 81 and 82 may be connected to the ground separately from each other. Alternatively, all of the ground terminals 5a and 5b and the metal housings 81 and 82 may be connected to the same connection point (i.e., connected to one connection point) by using soldering or the like and then connected to the ground. Further, the windings 6a and 6b may be connected in series.

In such a case, capacitive coupling formed between the windings 6a and 6b can be cut off. Further, since capacities are formed between the winding 6a and the metal housing 81 and between the winding 6b and the metal housing 82, the damping characteristic of the noise filter 100 can be further improved. Note that the structure and the like of the housings may be modified according to the permissible values for the leak current, the resonance frequency, and the damping characteristic required for the noise filter.

Further, when the noise filter 100 includes three or more inductor elements, the noise filter 100 may further include three or more metal housings that house the respective inductor elements.

Figure 23:
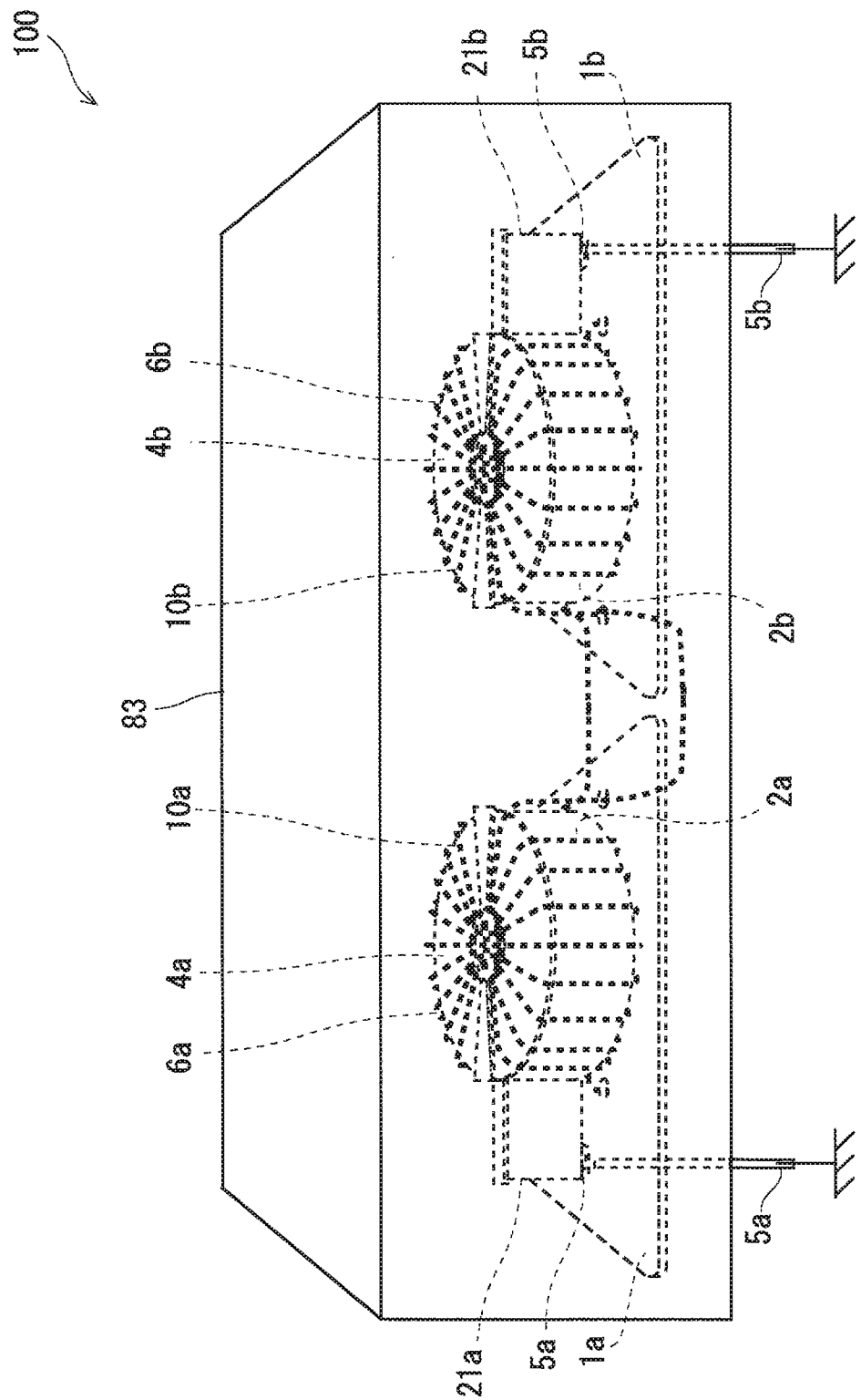
FIG. 23 is a perspective view of a modified example of the noise filter according to the first exemplary embodiment.

Further, as shown in FIG. 23, the noise filter 100 may further include a metal housing 83 that houses both of the inductor elements 10a and 10b. Specifically, the metal housing 83 houses the inductor elements 10a and 10b and the pedestals 1a and 1b. When the noise filter 100 includes the metal housing 83, the ground terminals 5a and 5b and the metal housing 83 may be connected to the ground separately from each other. Alternatively, all of the ground terminals 5a and 5b and the metal housing 83 may be connected to the same connection point (i.e., connected to one connection point) by using soldering or the like and then connected to the ground. Further, the windings 6a and 6b may be connected in series.

In such a case, since a capacity is formed between the metal housing 83 and the windings 6a and 6b, the damping characteristic of the noise filter 100 can be further improved. Note that the structure and the like of the housing may be modified according to the permissible values for the leak current, the resonance frequency, and the damping characteristic required for the noise filter.

Further, the noise filter according to any of the second to seventh exemplary embodiments may further include one metal housing that houses all of a plurality of inductor elements as in the case of the noise filter 100 shown in FIG. 23.

EXPERIMENTS

Next, we have carried out various experiments for various noise filters. These experiments are explained hereinafter.

Reference Experiment 1

Damping characteristics of noise filters including inductor elements having no ground terminal were evaluated. Further, a method for calculating a damping characteristic was also evaluated.

Firstly, values of an S-parameter (scattering parameter) S21 over a frequency band were measured for Comparative Example 1 and Reference Example 1.

Comparative Example 1 was a noise filter having a configuration identical to that of the noise filter 100 (see FIGS. 1A and 2) except that the ground terminals 5a and 5b were omitted (i.e., removed).

Reference Example 1 was a noise filter having a configuration identical to that of the noise filter used in Comparative Example 1 except that Reference Example 1 included only one of the inductor elements 10a and 10b. In other words, Reference Example 1 was a noise filter including only one inductor element having no ground terminal and Comparative Example 1 was a noise filter that was obtained by arranging two inductor elements each of which was identical to that used in Reference Example 1 side by side and connecting them with each other in series.

Further, values of the S-parameter $S_{21}$ over frequencies of the noise filter corresponding to Comparative Example 1 were calculated by multiplexing impedances in Reference Example 1 by a factor of two. The result of this calculation is referred to as a "Calculation Example 1".

Figure 24:
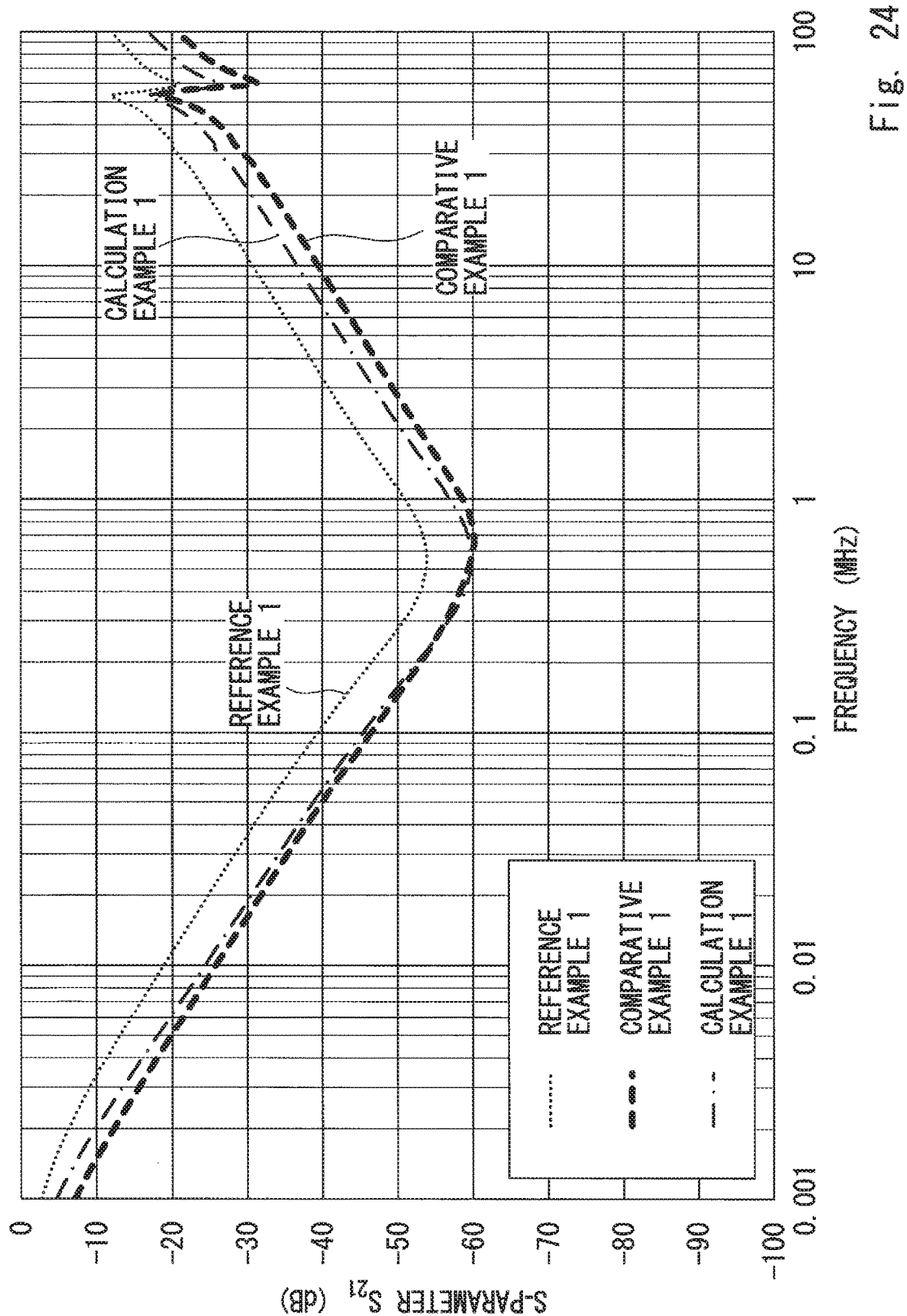
FIG. 24 is a graph showing values of an S-parameter $S_{21}$ over frequencies.

FIG. 24 shows measurement results of Comparative Example 1 and Reference Example 1, and calculation results of Calculation Example 1. As shown in FIG. 24, the values of Calculation Example 1 were substantially equal to those of Comparative Example 1. This means that it is possible to obtain measurement values of a noise filter in which two inductor elements are arranged side by side from measurement results of a noise filter including only one inductor element by using the calculation method used for Calculation Example 1.

Experiment 1

Next, a damping characteristic of a noise filter according to the first exemplary embodiment was evaluated. Further, a method for calculating a damping characteristic was also evaluated.

Firstly, values of the S-parameter $S_{21}$ over a frequency band were measured for Example 1 and Reference Example 2.

Example 1 was a noise filter having a configuration identical to that of the noise filter 100 (see FIGS. 1A and 2). As for the magnetic core, a magnetic core made of material having a permeability of about 10,000 was used. The magnetic core had a toroidal shape and its size was as follows: the outer diameter was 22 mm; the inner diameter was 14 mm; and the height was 10 mm. The ground terminal had such a structure that a ground end having a length of 11.43 mm and a width of 2.8 mm protruded in an L-shape from one end of the central part having a length of 78.45 mm and a width of 7 mm. The ground terminal had such a structure that the central part was wound around the magnetic core. As the winding, each of two Class-1 polyurethane-coated copper wires each having a diameter of 0.6 mmφ was wound around the insulating case and the insulating cap, in which the magnetic core and the ground terminal were contained, 44 times. The capacitance formed between the winding and the ground terminal was 20 pF. Note that components used in the other Examples, Reference Examples, and Comparative Examples that were in common with those in Example 1 were identical to those in Example 1.

Reference Example 2 was a noise filter having a configuration identical to that of the noise filter used in Example 1 except that Reference Example 2 included only one of the inductor elements 10a and 10b. In other words, Reference Example 2 was a noise filter including only one of the inductor elements 10a and 10b and Example 1 was a noise filter that was obtained by arranging two inductor elements each of which was identical to that used in Reference Example 2 side by side and connecting them with each other in series.

Further, similarly to Calculation Example 1, values of the S-parameter $S_{21}$ over frequencies of the noise filter corresponding to Example 1 were calculated by multiplexing impedances in Reference Example 2 by a factor of two. The result of this calculation is referred to as a "Calculation Example 2".

Figure 12:
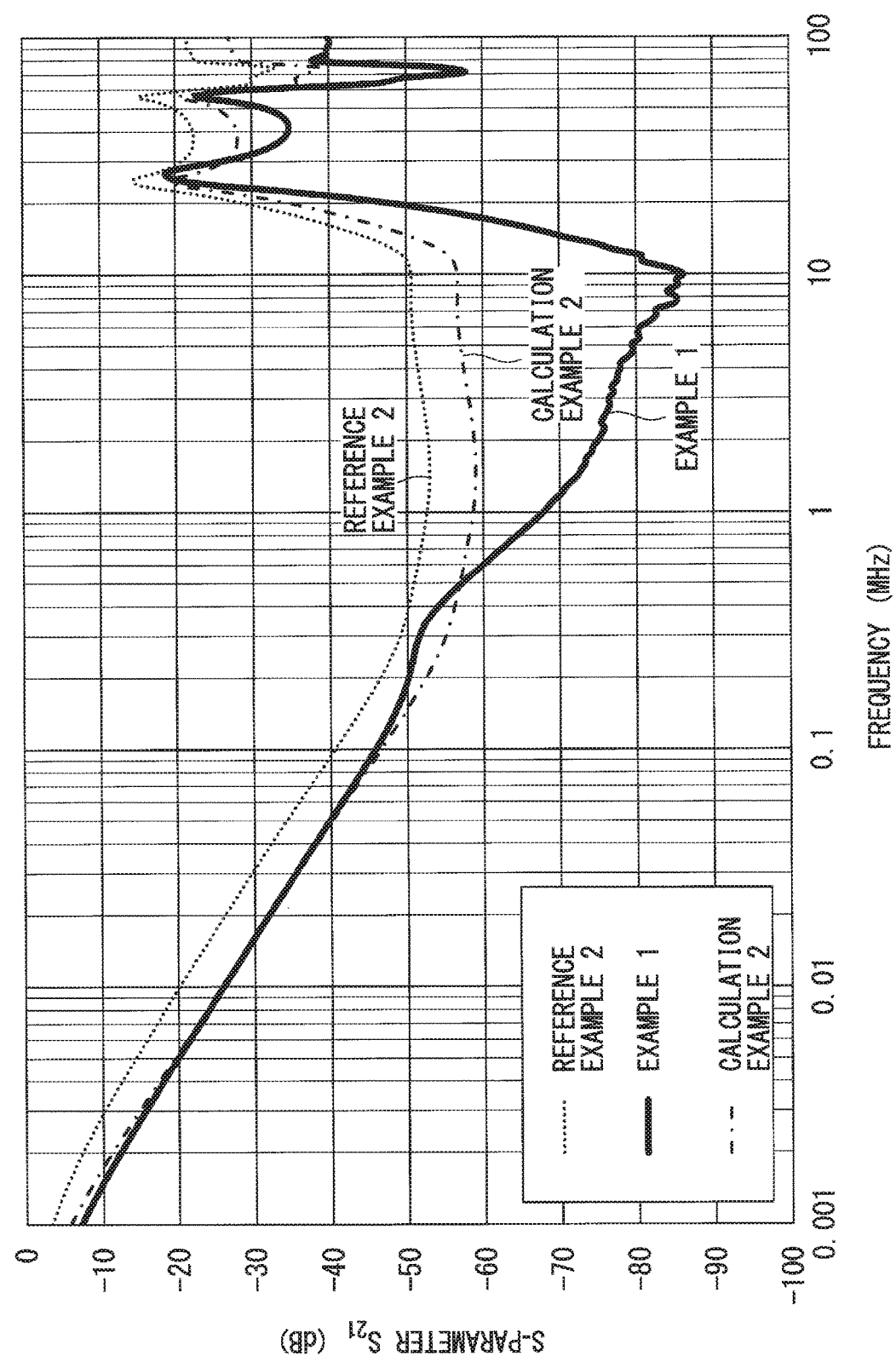
FIG. 12 is a graph showing values of an S-parameter $S_{21}$ over frequencies.

FIG. 12 shows measurement results of Reference Example 2 and Example 1, and calculation results of Calculation Example 2. As shown in FIG. 12, in Example 1 and Calculation Example 2, the S-parameter $S_{21}$ was low in a frequency band between about 1.0 and 10 MHz. Compared to Calculation Example 2, Example 1 exhibited a high damping characteristic in a frequency range of about 1.0 to 10 MHz. This means that when the calculation method used for Calculation Example 2 was used, measurement values (or values close thereto) of the noise filter in which two inductor elements were arranged side by side (Example 1) could not be obtained from measurement results of the noise filter including only one inductor element (Reference Example 2). One of the possible reasons for this is that the noise filter used in Example 1 performed a function of dissipating the common-mode noise from the inside of the inductors into the ground.

Experiment 2

Next, evaluation results of damping characteristics of Example 1 and a two-stage-connection LC filter are explained hereinafter. Specifically, values of the S-parameter $S_{21}$ over a frequency band were measured for Comparative Examples 2 to 4.

Each of Comparative Examples 2 to 4 was a two-stage-connection LC filter (also expressed as a "L-C-L-C" filter) formed by connecting a noise filter used in Reference Example 1 (see FIG. 24), a Y-capacitor C, another noise filter used in Reference Example 1, and another Y-capacitor C with one another in series in this listed order. Each of the Y-capacitors C used in Comparative Example 2 had a capacitance of 100 pF and each of the Y-capacitors C used in Comparative Example 3 had a capacitance of 220 pF. Further, each of the Y-capacitors C used in Comparative Example 4 had a capacitance of 470 pF. Meanwhile, the capacitance formed between the winding and the ground terminal in Example 1 was 20 pF and hence smaller than the capacitances of the Y-capacitors C used in Comparative Examples 2 to 4. Then number of components of Example 1 is smaller than that of each of Comparative Examples 2 to 4.

Figure 13:
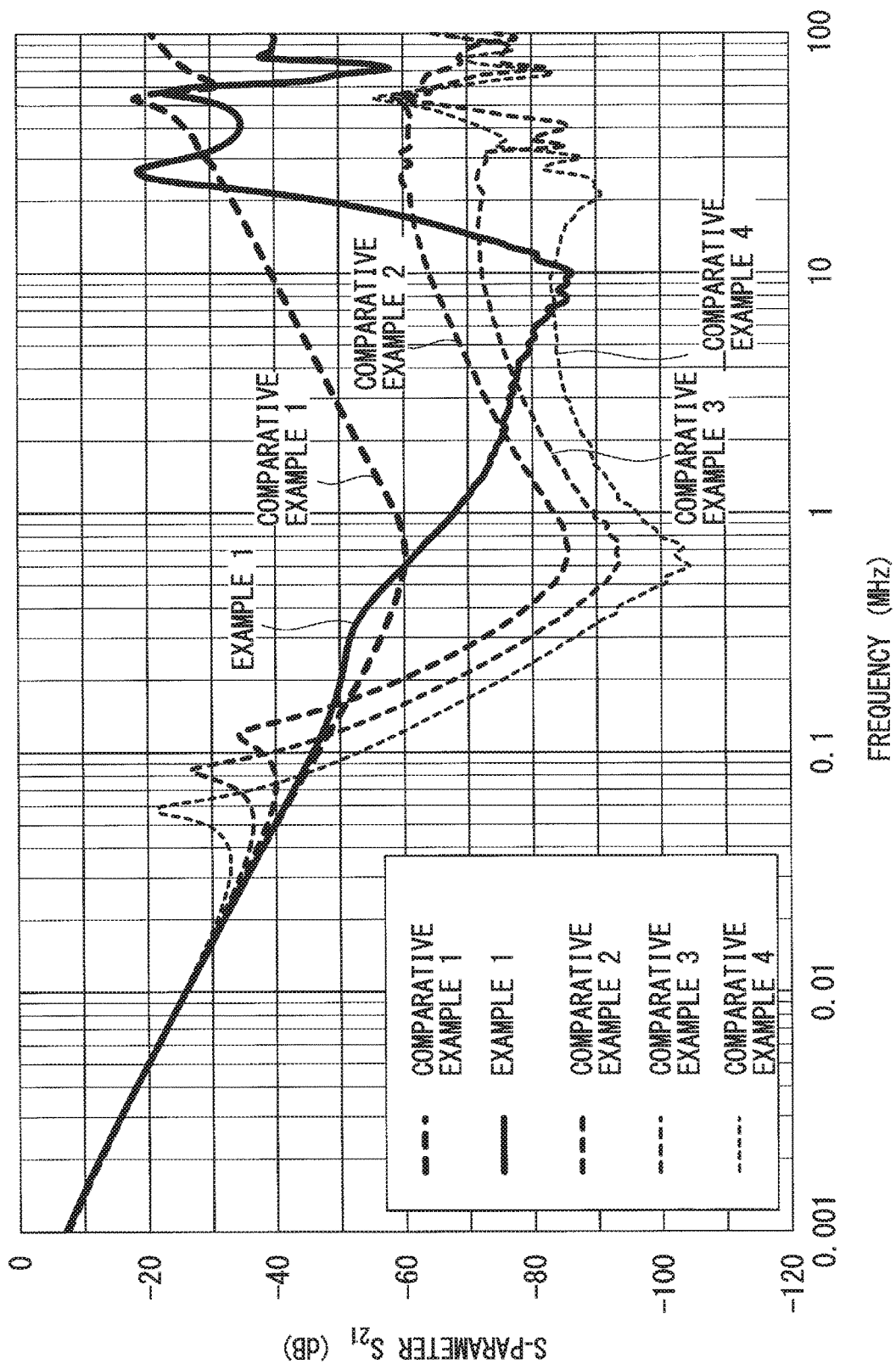
FIG. 13 is a graph showing values of an S-parameter $S_{21}$ over frequencies.

FIG. 13 shows measurement results of the S-parameter $S_{21}$ over a frequency band for Comparative Examples 2 to 4 and measurement results of Example 1 and Comparative Example 1.

As shown in FIG. 13, in Example 1, values of the S-parameter $S_{21}$ in a certain range in a frequency band between 1 and 10 MHz were roughly equal to those in Comparative Examples 2 to 4. Therefore, depending on the frequency band, Example 1 had a damping characteristic roughly equivalent to those of Comparative Examples 2 to 4, which were two-stage-connection LC filters. Meanwhile, the capacitance formed between the winding and the ground terminal in Example 1 was smaller than those of Comparative Examples 2 to 4. One of the possible reasons for this is that the ground terminal performed a function of dissipating the common-mode noise from the inside of the inductors into the ground in Example 1.

Experiment 3

Figure 14:
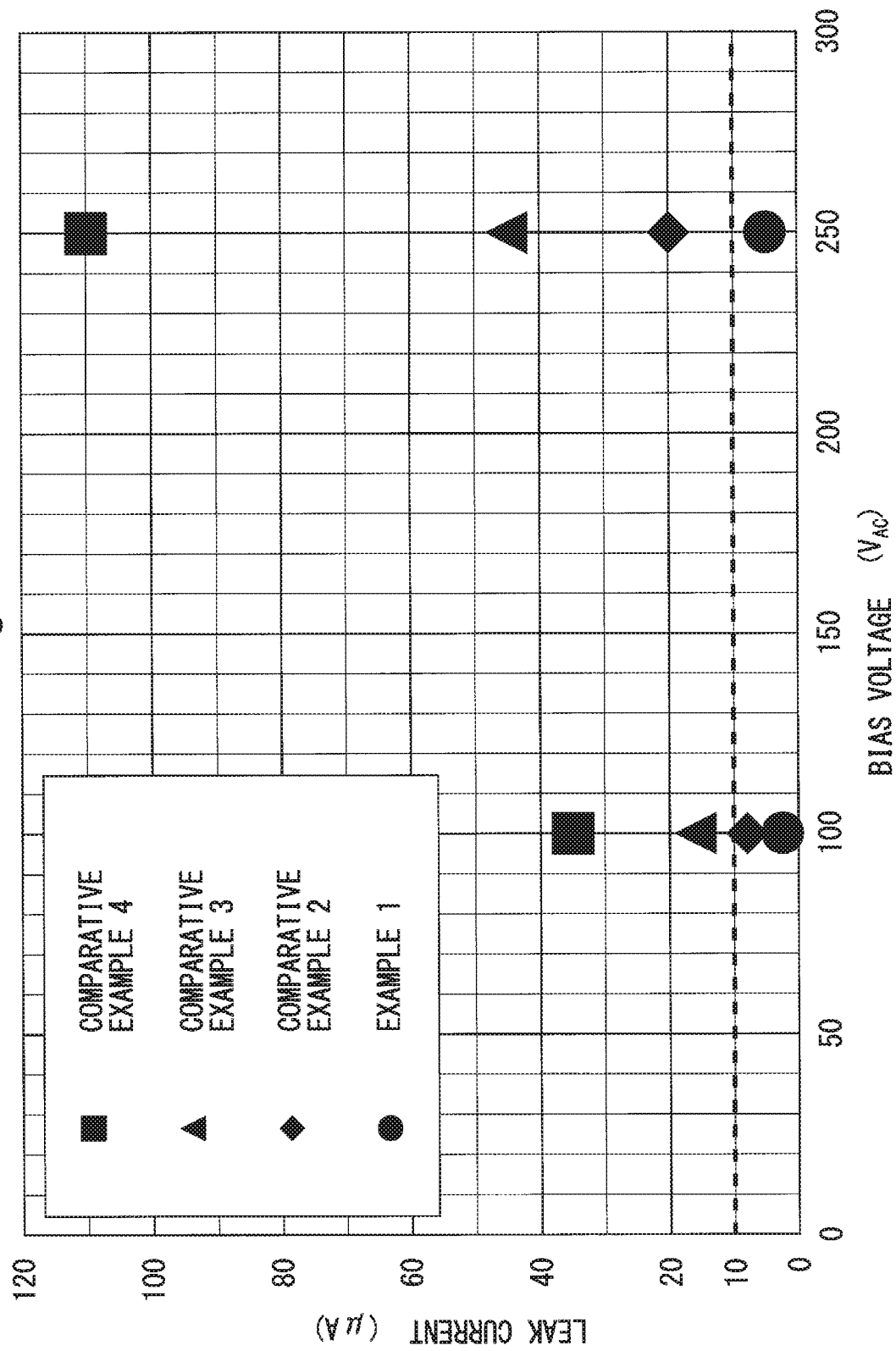
FIG. 14 is a graph showing leak currents over bias voltages.

Next, measurement results of a leak current for Example 1 and Comparative Examples 2 to 4 are explained with reference to FIG. 14. Note that the leak current is a current that flows between power supply line terminals and the ground when an AC (Alternating Current) bias voltage is continuously applied between the power supply line terminals. FIG. 14 shows measurement results of the leak current.

As shown in FIG. 14, in Example 1, the leak current was 10 μA or smaller in both of when the bias voltage was 100 $V_{AC}$ and when it was 250 $V_{AC}$. In contrast to this, in Comparative Examples 2 to 4, the leak current often exceeded 10 μA. Therefore, the leak current in Example 1 was smaller than those in Comparative Examples 2 to 4. One of the possible reasons for this is that the capacitance formed between the winding and the ground terminal in Example 1 was lower than the capacitance of the Y-capacitor in Comparative Examples 2 to 4.

Incidentally, in medical instruments including a CF-type fitting part, the permissible value for the leak current is often 10 μA or smaller. It should be noted that the CF-type fitting part is a part that comes into direct contact with the heart (i.e., the heart of a human being). Therefore, since the noise filter according to Example 1 satisfies the permissible value for the leak current, it is preferably used for a medical instrument including a CF-type fitting part.

Experiment 4

Next, evaluation results of a damping characteristic of a noise filter having a configuration identical to that of the noise filter in Example 1 except that the permeability of the magnetic core differs from that in Example 1 are explained with reference to FIG. 15.

Each of Examples 2 and 3 was a noise filter having a configuration identical to that of the noise filter in Example 1 except that the permeability of the magnetic core differs from that in Example 1. In Example 2, as the magnetic core, an Mn—Zn ferrite core having a permeability of 5,000 was used. In Example 3, as the magnetic core, an Ni—Zn ferrite core having a permeability of 650 was used. Values of the S-parameter $S_{21}$ over a frequency band were measured for Examples 2 and 3, and FIG. 15 shows these measurement results and measurement results of Example 1.

Figure 15:
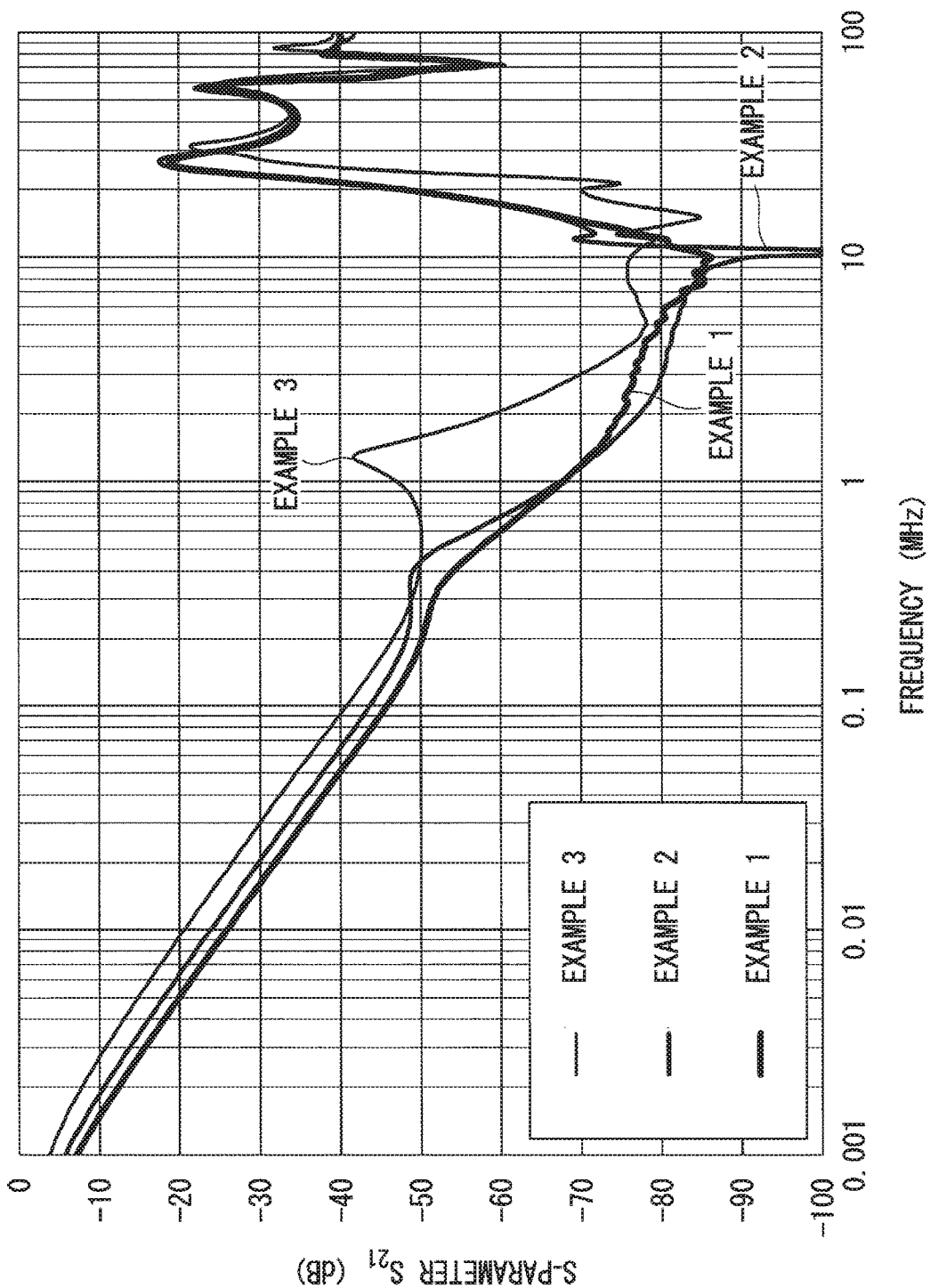
FIG. 15 is a graph showing values of an S-parameter $S_{21}$ over frequencies.

As shown in FIG. 15, the damping characteristic of Example 1 was the highest in a frequency band between about 0.001 to 1 MHz and the damping characteristic of Example 2 was the highest in a frequency band between about 1 MHz to about 7 MHz. Further, the damping characteristic of Example 3 was the highest in a frequency band between about 10 MHz to about 30 MHz.

Therefore, it is possible to obtain a noise filter having a desired damping characteristic by combining magnetic cores having different permeabilities according to the frequency band of the noise.

Experiment 5

Next, evaluation results of a damping characteristic of a two-stage-connection LC filter including a noise filter used in Example 1 are explained.

Specifically, values of the S-parameter $S_{21}$ over a frequency band were measured for Examples 4 to 6 and Comparative Examples 5 to 7.

Figure 16:
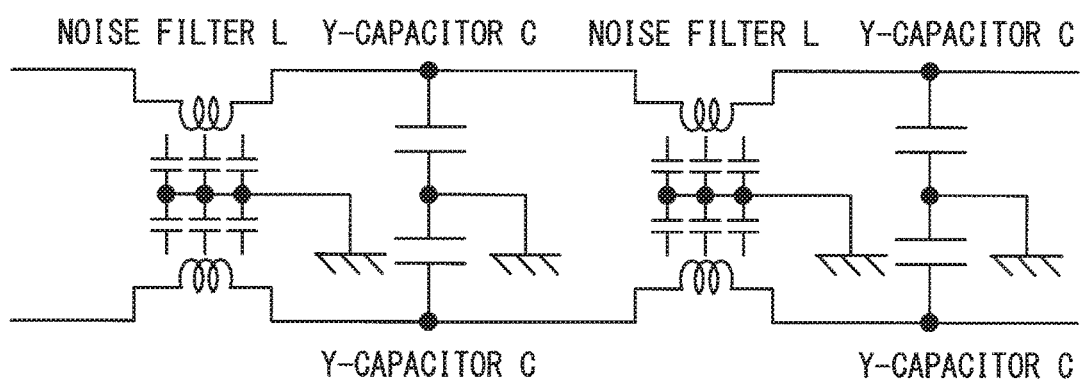
FIG. 16 is a connection diagram of a noise filter according to Examples 4 to 6.

Each of Examples 4 to 6 was a two-stage-connection LC filter obtained by connecting a noise filter (L) used in Reference Example 2, a Y-capacitor (C), another noise filter (L) used in Reference Example 2, and another Y-capacitor (C) with one another in series in this listed order. Each of the Y-capacitors (C) used in Example 4 had a capacitance of 100 pF and each of the Y-capacitors (C) used in Example 5 had a capacitance of 220 pF. Further, each of the Y-capacitors (C) used in Example 6 had a capacitance of 470 pF. As shown in FIG. 16, noise filters (L) used in Reference Example 2 and Y-capacitors (C) were connected with one another in each of Examples 4 to 6.

Figure 25:
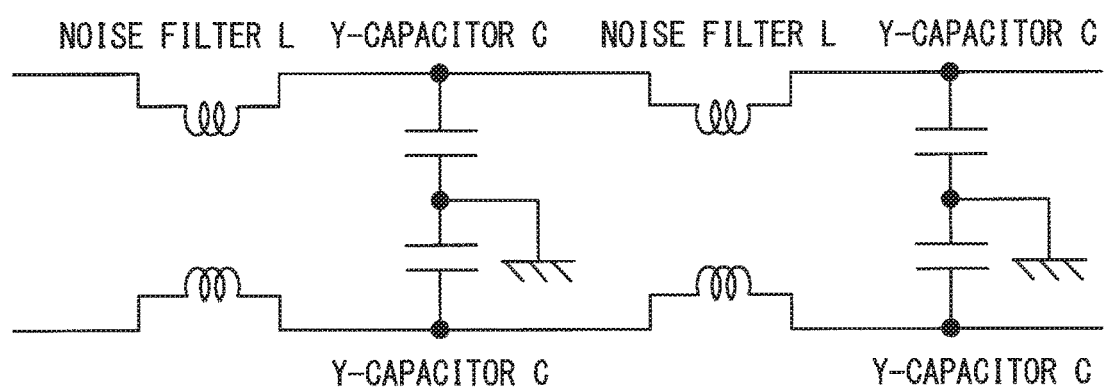
FIG. 25 is a connection diagram of a noise filter according to Comparative Examples 5 to 7.

Each of Comparative Examples 5 to 7 was a noise filter having a configuration identical to that of the noise filter in Examples 4 to 6 except that a noise filter used in Reference Example 1 was used instead of using the noise filter used in Reference Example 2. As shown in FIG. 25, noise filters (L) used in Reference Example 1 and Y-capacitors (C) were connected with one another in each of Comparative Examples 5 to 7.

Figure 17:
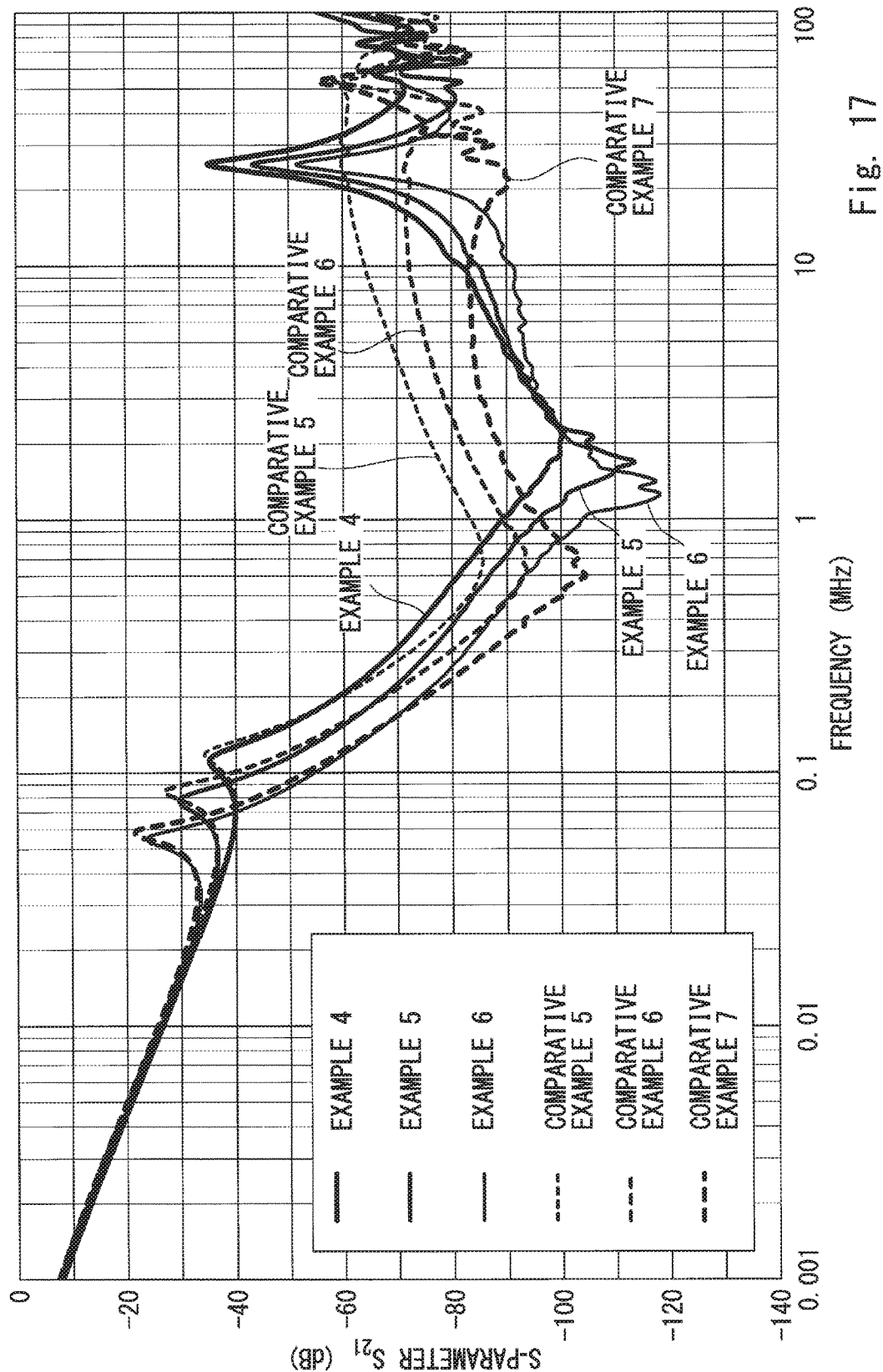
FIG. 17 is a graph showing values of an S-parameter $S_{21}$ over frequencies.

As shown in FIG. 17, the values of the S-parameter $S_{21}$ in a frequency band between about 1 and 10 MHz in Examples 4 to 6 were lower than those in Comparative Examples 5 to 7. That is, Examples 4 to 6 had high damping characteristics in the frequency band between about 1 and 10 MHz.

Therefore, the two-stage-connection LC filter including the noise filter used in Reference Example 2 had a higher damping characteristic than that of the two-stage-connection LC filter including the noise filter used in Reference Example 1.

Experiment 6

Next, evaluation results of a damping characteristic of a noise filter including three inductor elements are explained. The three inductor elements of this noise filter are connected with one another in series.

Specifically, values of the S-parameter $S_{21}$ over a frequency band were measured for Example 7. Example 7 was a noise filter having a configuration identical to that of the noise filter 500 (see FIG. 9). Further, similarly to Calculation Examples 1 and 2, values of the 5-parameter $S_{21}$ over frequencies of the noise filter corresponding to Example 7 were calculated by multiplexing impedances in Reference Example 2 by a factor of three. The result of this calculation is referred to as a "Calculation Example 3".

Figure 18:
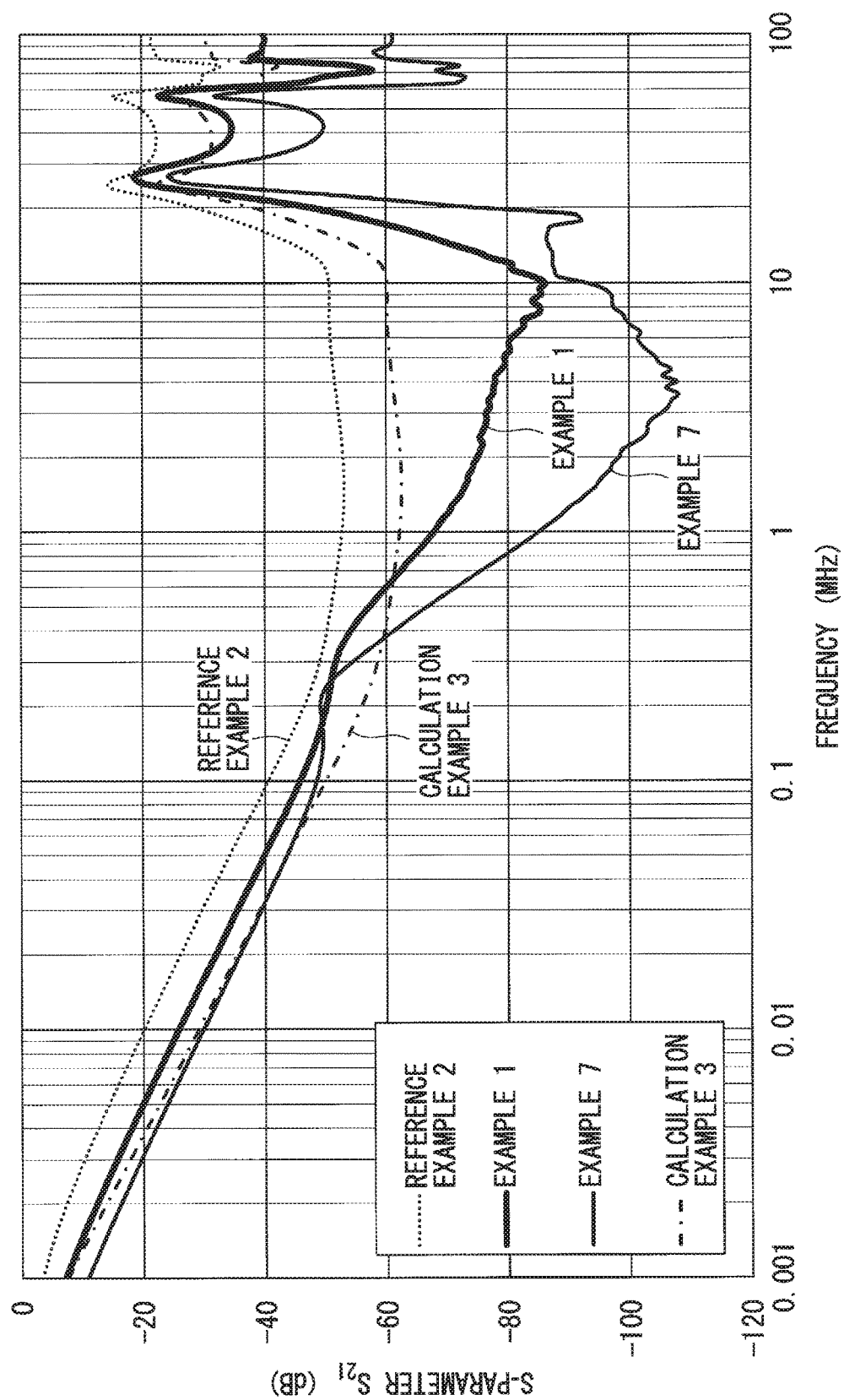
FIG. 18 is a graph showing values of an S-parameter $S_{21}$ over frequencies.

FIG. 18 shows measurement results of Example 1, Example 7, and Reference Example 2, and calculation results of Calculation Example 3. As shown in FIG. 18, the values of the S-parameter $S_{21}$ in a frequency band between about 0.5 and 20 MHz in Example 7 were lower than those of the S-parameter $S_{21}$ in Example 1 and Calculation Example 3. That is, Example 7 had a high damping characteristic in the frequency band between about 0.5 and 20 MHz.

Further, compared to Calculation Example 3, Example 7 exhibited a high damping characteristic in a frequency range of about 1.0 to 10 MHz. This means that when the calculation method used for Calculation Example 3 was used, it was very difficult to obtain measurement values of the noise filter in which three inductor elements were connected in series (Example 7) from measurement results of the noise filter including only one inductor element (Reference Example 2). Example 7 has a damping characteristic higher than predicted values calculated from the measurement results of Reference Example 2. One of the possible reasons for this is that the noise filter used in Example 7 performed a function of dissipating the common-mode noise from the inside of the inductors into the ground.

Further, Example 7 exhibited a high damping characteristic, which is higher than even Example 1. As shown in FIG. 13, depending on the frequency band, Example 1 has a damping characteristic roughly equivalent to those of Comparative Examples 2 to 4. Therefore, Example 7 can reproduce (i.e., simulate) a damping characteristic of a three-stage-connection LC filter. A three-stage-connection LC filter (also expressed as an "L-C-L-C-L-C" filter) is formed by connecting three pairs each consisting of a noise filter L and a Y-capacitor C with one another in series. Further, it is considered that a noise filter in which four or more inductor elements are connected in series has a high damping characteristic as in the case of Example 7.

Experiment 7

Next, damping characteristics of noise filters each including two inductor elements stacked on one another were evaluated.

Specifically, values of the S-parameter $S_{21}$ over a frequency band were measured for Examples 8 and 9 were measured. Example 8 was a noise filter having a configuration identical to that of the noise filter 600 (see FIG. 10) except that it does not includes the ground conductor plate 7. Example 9 was a noise filter having a configuration identical to that of the noise filter 700 (see FIG. 11) except that it does not includes the ground conductor plate 7.

Figure 19:
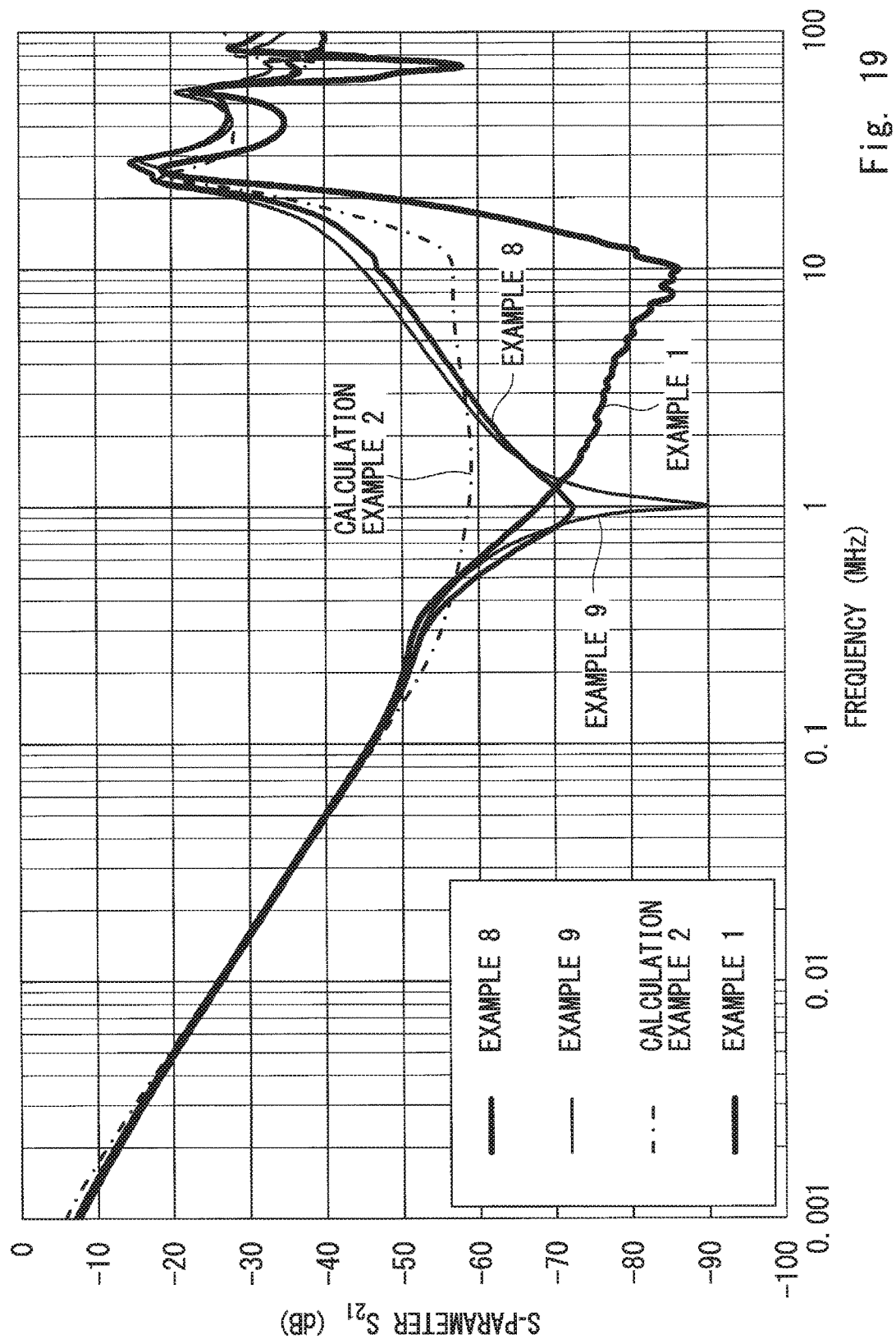
FIG. 19 is a graph showing values of an S-parameter $S_{21}$ over frequencies.

FIG. 19 shows measurement results of these Examples 8 and 9 and Example 1, and calculation results of Calculation Example 2.

As shown in FIG. 19, in Examples 8 and 9, the S-parameter $S_{21}$ was low in a certain frequency band, in particular, a certain frequency band around 1 MHz compared to Calculation Example 2. That is, Examples 8 and 9 exhibited a high damping characteristic in the frequency band around 1 MHz compared to Calculation Example 2. Further, in Examples 8 and 9, the S-parameter $S_{21}$ had its bottom (i.e., the lowest part) in a frequency band different from that of Example 1. One of the possible reasons for this is that a current that conducts capacitive coupling between the coil of one of the inductor elements and the coil of the other inductor element occurred.

Experiment 8

Next, damping characteristics of noise filters each including two inductor elements stacked on one another in the vertical direction were evaluated.

Specifically, values of the S-parameter $S_{21}$ over a frequency band were measured for Example 10 and Comparative Example 8 were measured.

Example 10 was a noise filter having a configuration identical to that of the noise filter 600 (see FIG. 10). Comparative Example 8 was a noise filter having a configuration identical to that of the noise filter 600 except that it does not include the ground terminal.

Figure 20:
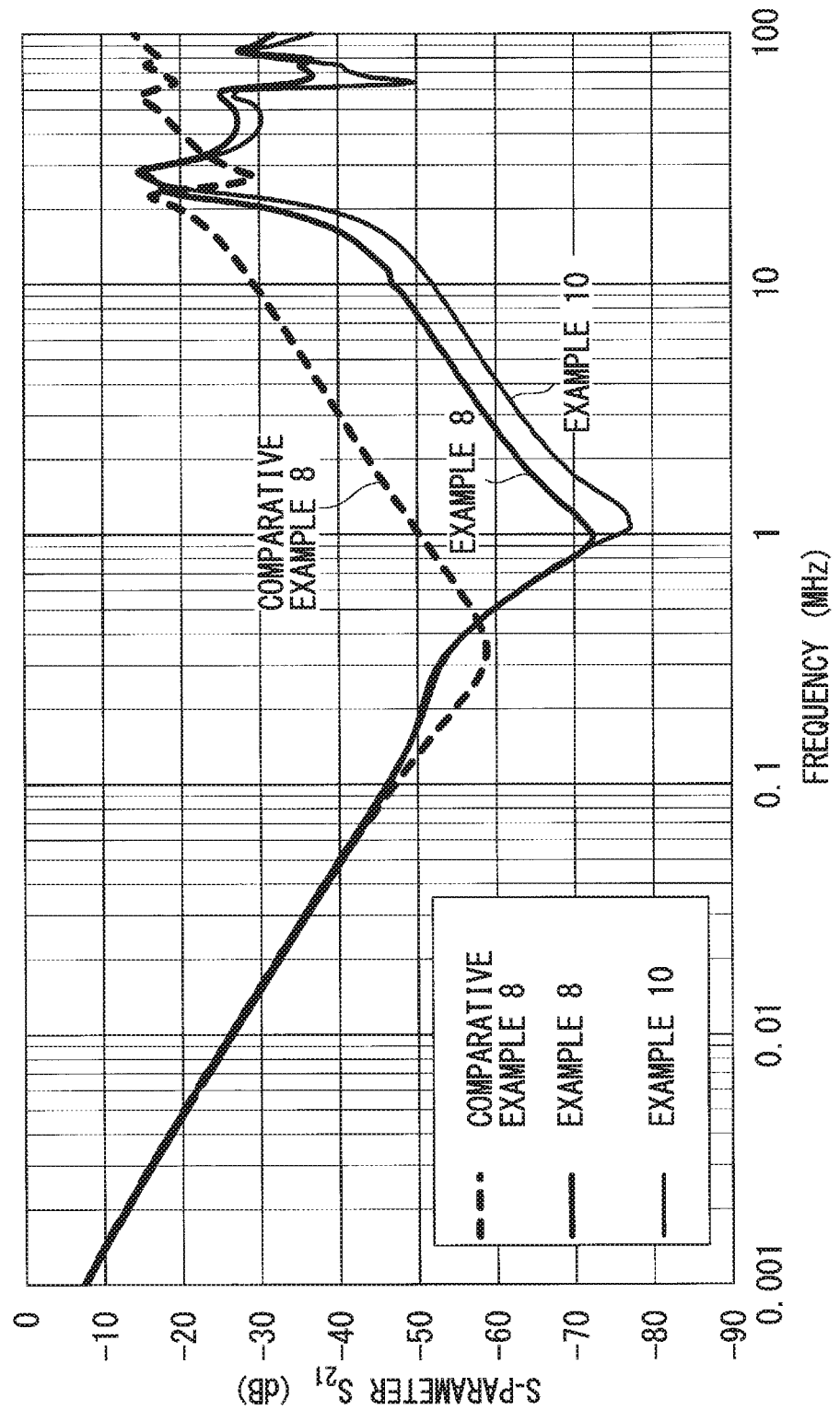
FIG. 20 is a graph showing values of an S-parameter $S_{21}$ over frequencies.

FIG. 20 shows measurement results of these Example 10 and Comparative Example 8, and Example 8.

As shown in FIG. 20, the values of the S-parameter $S_{21}$ in Example 10 were lower than those of the S-parameter $S_{21}$ in Comparative Example 8. That is, Example 10 exhibited a damping characteristic higher than that of Comparative Example 8. Further, in Example 10, the S-parameter $S_{21}$ had its bottom (i.e., the lowest part) in a frequency band slightly different from that of Example 8.

Experiment 9

Next, damping characteristics of noise filters each including two inductor elements stacked on one another in a horizontal direction were evaluated.

Specifically, values of the S-parameter $S_{21}$ over a frequency band were measured for Example 11 and Comparative Example 9 were measured.

Example 11 was a noise filter having a configuration identical to that of the noise filter 700 (see FIG. 11).

Comparative Example 9 was a noise filter having a configuration identical to that of the noise filter 700 except that it does not include the ground terminal.

Figure 21:
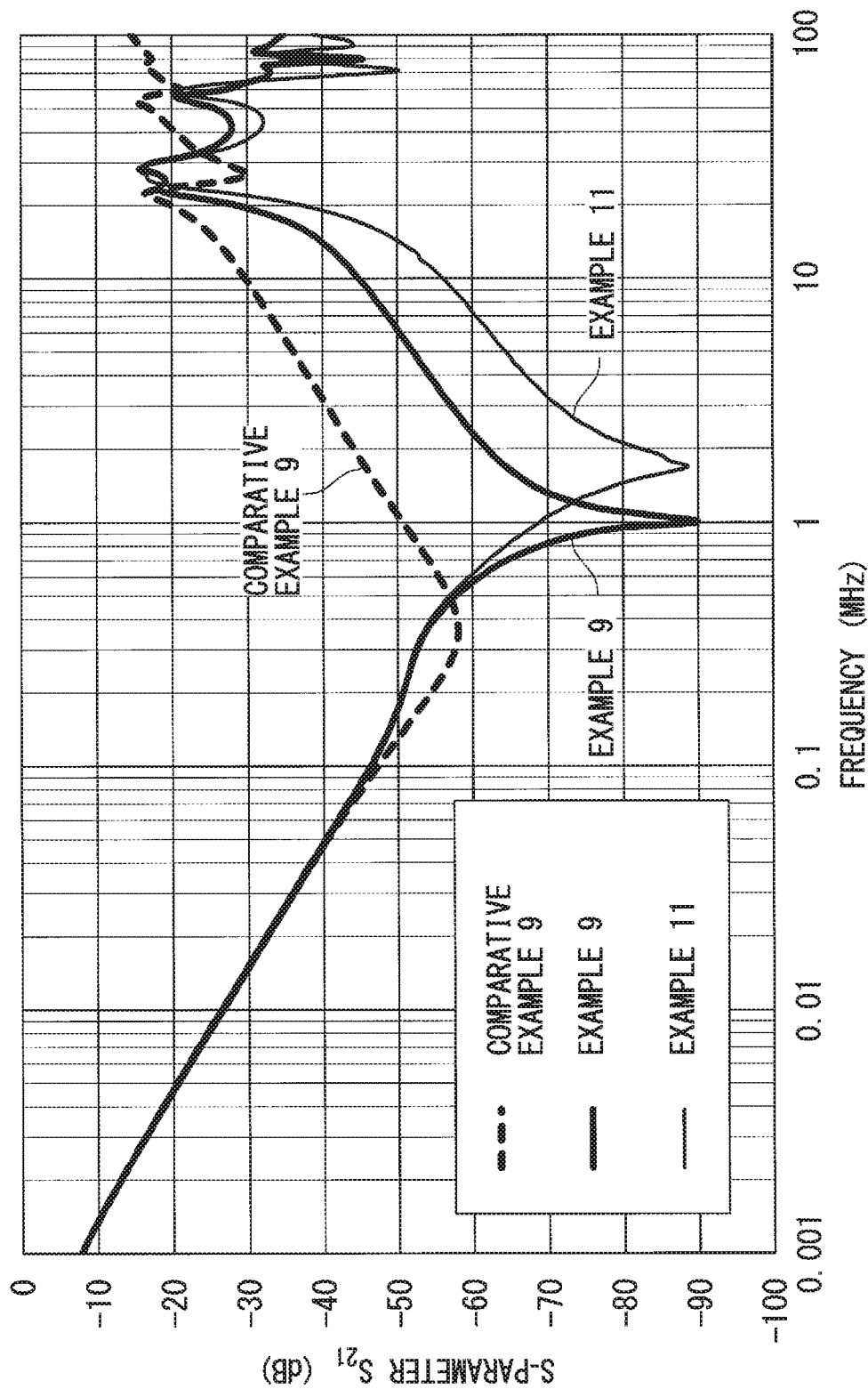
FIG. 21 is a graph showing values of an S-parameter $S_{21}$ over frequencies.

FIG. 21 shows measurement results of these Example 11 and Comparative Example 9, and Example 9.

As shown in FIG. 21, the values of the S-parameter $S_{21}$ in Example 11 were lower than those of the S-parameter $S_{21}$ in Comparative Example 9. That is, Example 11 exhibited a damping characteristic higher than that of Comparative Example 9. Further, in Example 11, the S-parameter $S_{21}$ had its bottom (i.e., the lowest part) in a frequency band different from that of Example 1. One of the possible reasons for this is that even if a current that conducts capacitive coupling between the coil of one of the inductor elements and the coil of the other inductor element occurred, the capacitive coupling was cut off by the presence of the ground conductor plate interposed between the inductor elements and hence the signal was attenuated (i.e., dumped).

The present invention has been explained above with the above-described exemplary embodiments and examples. However, the present invention is not limited to the above-described exemplary embodiments and examples, and needless to say, various modifications, corrections, and combinations that can be made by those skilled in the art are also included in the scope of the present invention specified in the claims of the present application.

From the invention thus described, it will be obvious that the embodiments of the invention may be varied in many ways. Such variations are not to be regarded as a departure from the spirit and scope of the invention, and all such modifications as would be obvious to one skilled in the art are intended for inclusion within the scope of the following claims.

What is claimed is:

1. A noise filter comprising a plurality of inductor elements connected with one another in series, wherein
    each of the inductor elements comprises: a ring-shaped magnetic core; a winding wound around the magnetic core; a ground terminal disposed between the magnetic core and the winding, the ground terminal being connected to a ground, and a case housing the magnetic core and the ground terminal,
    the ground terminal comprises a conductive part that surrounds at least a part of an outer periphery of the magnetic core, and
    the conductive part and the magnetic core are electrically insulated from each other by a groove into which the conductive part is inserted on the inner side of the case.

2. A noise filter comprising a plurality of inductor elements connected with one another in series, wherein
    each of the inductor elements comprises: a ring-shaped magnetic core; a winding wound around the magnetic core; and a ground terminal disposed between the magnetic core and the winding, the ground terminal being connected to a ground,
    the ground terminal comprises a conductive part that surrounds at least a part of an outer periphery of the magnetic core, and
    each of the plurality of inductor elements is disposed on a respective one of a plurality of support members.

3. The noise filter according to claim 1, wherein the plurality of inductor elements are arranged in a row in one direction on one support member.

4. The noise filter according to claim 1, wherein the plurality of magnetic cores, each of which is included in a respective one of the plurality of inductor elements, are arranged in a row, and
    the conductive part of the one ground terminal surrounds at least a part of the plurality of magnetic cores arranged in a row.

5. A noise filter comprising a plurality of inductor elements connected with one another in series, wherein
    each of the inductor elements comprises: a ring-shaped magnetic core; a winding wound around the magnetic core; and a ground terminal disposed between the magnetic core and the winding, the ground terminal being connected to a ground,
    the ground terminal comprises a conductive part that surrounds at least a part of an outer periphery of the magnetic core, and
    the plurality of inductor elements are stacked on one another on one support member.

6. The noise filter according to claim 5, wherein the plurality of inductor elements sandwich a ground conductor plate therebetween.

7. The noise filter according to claim 1, wherein each of the plurality of inductor elements is housed in a respective one of a plurality of metal housings.

8. The noise filter according to claim 1, wherein the plurality of inductor elements are housed in one metal housing.

9. A multistage-connection LC filter comprising: a plurality of noise filters and a plurality of Y-capacitors, wherein
    the plurality of noise filters comprise a plurality of inductor elements connected with one another in series,
    each of the inductor elements comprises: a ring-shaped magnetic core; a winding wound around the magnetic core; a ground terminal disposed between the magnetic core and the winding, the ground terminal being connected to a ground, and a case housing the magnetic core and the ground terminal,
    the ground terminal comprises a conductive part that surrounds at least a part of an outer periphery of the magnetic core,
    the conductive part and the magnetic core are electrically insulated from each other by a groove into which the conductive part is inserted on the inner side of the case, and
    the plurality of inductor elements and the plurality of Y-capacitors are alternately connected in series.

10. A medical instrument comprising a multistage-connection LC filter according to claim 9.

11. A multistage-connection LC filter comprising: a plurality of noise filters and a plurality of Y-capacitors, wherein
    the plurality of noise filters comprising a plurality of inductor elements connected with one another in series, wherein
    each of the inductor elements comprises: a ring-shaped magnetic core; a winding wound around the magnetic core; and a ground terminal disposed between the magnetic core and the winding, the ground terminal being connected to a ground,
    the ground terminal comprises a conductive part that surrounds at least a part of an outer periphery of the magnetic core, and
    each of the plurality of inductor elements is disposed on a respective one of a plurality of support members, and
    the plurality of inductor elements and the plurality of Y-capacitors are alternately connected in series.

12. A multistage-connection LC filter comprising: a plurality of noise filters and a plurality of Y-capacitors, wherein
    the plurality of noise filters comprising a plurality of inductor elements connected with one another in series, wherein
    each of the inductor elements comprises: a ring-shaped magnetic core; a winding wound around the magnetic core; and a ground terminal disposed between the magnetic core and the winding, the ground terminal being connected to a ground,
    the ground terminal comprises a conductive part that surrounds at least a part of an outer periphery of the magnetic core, and
    the plurality of inductor elements are stacked on one another on one support member, and the plurality of inductor elements and the plurality of Y-capacitors are alternately connected in series.

* * * * *

UNITED STATES PATENT AND TRADEMARK OFFICE
CERTIFICATE OF CORRECTION

PATENT NO.        : 10,192,676 B2
APPLICATION NO.   : 15/173277
DATED             : January 29, 2019
INVENTOR(S)       : Yusuke Ohdaira It is certified that error appears in the above-identified patent and that said Letters Patent is hereby corrected as shown below:

On the Title Page

Change Assignee to:
--TOKIN CORPORATION--

Signed and Sealed this
Nineteenth Day of February, 2019

Andrei Iancu
*Director of the United States Patent and Trademark Office*